United States Patent
Hu et al.

(10) Patent No.: US 10,253,297 B2
(45) Date of Patent: Apr. 9, 2019

(54) STEM CELL AGGREGATES AND METHODS FOR MAKING AND USING

(71) Applicants: Regents of the University of Minnesota, Minneapolis, MN (US); Katholieke Universiteit Leuven, Leuven (BE)

(72) Inventors: Wei-Shou Hu, Falcon Heights, MN (US); Kartik Subramanian, Northborough, MN (US); Catherine M. Verfaillie, Leuven (BE)

(73) Assignees: Regents of the University of Minnesota, Minneapolis, MN (US); Katholieke Universiteit Leuven, Leuven (BE)

( * ) Notice: Subject to any disclaimer, the term of this patent is extended or adjusted under 35 U.S.C. 154(b) by 640 days.

(21) Appl. No.: 13/889,015

(22) Filed: May 7, 2013

(65) Prior Publication Data
US 2013/0315882 A1 Nov. 28, 2013

Related U.S. Application Data

(63) Continuation of application No. 12/863,015, filed as application No. PCT/US2009/031528 on Jan. 21, 2009, now abandoned.

(60) Provisional application No. 61/022,121, filed on Jan. 18, 2008.

(51) Int. Cl.
| | | |
|---|---|---|
| *A01N 63/00* | (2006.01) | |
| *C12N 5/00* | (2006.01) | |
| *C12N 5/071* | (2010.01) | |
| *C12N 5/074* | (2010.01) | |
| *A01K 67/00* | (2006.01) | |
| *A61K 35/12* | (2015.01) | |

(52) U.S. Cl.
CPC .......... *C12N 5/067* (2013.01); *C12N 5/0607* (2013.01); *C12N 5/0671* (2013.01); *A61K 35/12* (2013.01); *C12N 2500/02* (2013.01); *C12N 2501/11* (2013.01); *C12N 2501/135* (2013.01); *C12N 2501/235* (2013.01); *C12N 2503/02* (2013.01); *C12N 2506/03* (2013.01)

(58) Field of Classification Search
CPC .... C12N 5/067; C12N 5/0607; C12N 5/0671; A61K 35/12
See application file for complete search history.

(56) References Cited

U.S. PATENT DOCUMENTS

| | | |
|---|---|---|
| 5,486,359 A | 1/1996 | Caplan et al. |
| 5,827,735 A | 10/1998 | Young et al. |
| 6,090,625 A | 7/2000 | Abuljadayel |
| 6,589,728 B2 * | 7/2003 | Csete et al. ............... 435/4 |
| 6,653,134 B2 | 11/2003 | Prockop et al. |
| 6,777,231 B1 | 8/2004 | Katz et al. |
| 7,015,037 B1 | 3/2006 | Furcht et al. |
| 7,045,148 B2 | 5/2006 | Hariri |
| 7,056,738 B2 | 6/2006 | Prockop et al. |
| 7,229,827 B2 | 6/2007 | Kim et al. |
| 7,311,905 B2 | 12/2007 | Hariri |
| 7,659,118 B2 | 2/2010 | Furcht et al. |
| 7,807,461 B2 | 10/2010 | Kang et al. |
| 7,838,289 B2 | 11/2010 | Furcht et al. |
| 7,883,892 B2 | 2/2011 | Verfaillie et al. |
| 7,927,587 B2 | 4/2011 | Blazer et al. |
| 8,075,881 B2 | 12/2011 | Verfaillie et al. |
| 8,147,824 B2 | 4/2012 | Maziarz et al. |
| 8,192,348 B2 | 6/2012 | Tranquillo et al. |
| 8,252,280 B1 | 8/2012 | Verfaillie et al. |
| 8,409,859 B2 | 4/2013 | Verfaillie et al. |
| 8,426,200 B2 | 4/2013 | Verfaillie et al. |
| 8,580,249 B2 | 11/2013 | Blazar et al. |
| 8,609,406 B2 | 12/2013 | Subramanian et al. |
| 8,609,412 B2 | 12/2013 | Panoskaltsis-Mortari et al. |
| 2001/0033834 A1 | 10/2001 | Wilkison et al. |
| 2001/0046489 A1 | 11/2001 | Habener et al. |
| 2002/0061587 A1 | 5/2002 | Anversa |
| 2002/0164794 A1 | 11/2002 | Wernet |
| 2003/0003090 A1 | 1/2003 | Prockop et al. |
| 2003/0032179 A1 | 2/2003 | Hariri |
| 2003/0059414 A1 | 3/2003 | Ho et al. |
| 2003/0119107 A1 | 6/2003 | Dang |
| 2004/0224401 A1 * | 11/2004 | Ludwig et al. ............. 435/366 |
| 2004/0235165 A1 | 11/2004 | Prockop et al. |
| 2005/0076396 A1 | 4/2005 | Katz et al. |
| 2005/0169896 A1 | 8/2005 | Li et al. |

(Continued)

FOREIGN PATENT DOCUMENTS

| | | |
|---|---|---|
| JP | 2001-521380 A | 6/2001 |
| WO | WO 96/23870 | 8/1996 |

(Continued)

OTHER PUBLICATIONS

Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of Islet beta-cells in the pancreas" Microscopy Research and Technique: 43:332-336 (1998).

(Continued)

*Primary Examiner* — Quang Nguyen
(74) *Attorney, Agent, or Firm* — Tarolli, Sundheim, Covell & Tummino LLP

(57) ABSTRACT

The invention is directed to compositions of cell aggregates and methods for making and using the cell aggregates where the aggregates comprise cells that are not embryonic stem cells but can differentiate into cell types of at least two of ectodermal, undo dermal, and mesodermal embryonic germ layers, e.g., stem cells.

12 Claims, 13 Drawing Sheets

(56) References Cited

U.S. PATENT DOCUMENTS

| | | | |
|---|---|---|---|
| 2005/0181502 A1 | 8/2005 | Furcht et al. | |
| 2006/0068496 A1 | 3/2006 | Kelly | |
| 2006/0177925 A1 | 8/2006 | Rosenberg et al. | |
| 2006/0228798 A1 | 10/2006 | Verfaillie et al. | |
| 2008/0194024 A1 | 8/2008 | Mays | |
| 2008/0311084 A1 | 12/2008 | Verfaillie et al. | |
| 2008/0317740 A1 | 12/2008 | Blazar et al. | |
| 2009/0018033 A1 | 1/2009 | Morgan et al. | |
| 2009/0104159 A1 | 4/2009 | Prosper et al. | |
| 2009/0104163 A1 | 4/2009 | Deans et al. | |
| 2009/0130065 A1* | 5/2009 | Xu et al. | 424/93.7 |
| 2009/0203129 A1 | 8/2009 | Furcht et al. | |
| 2009/0203130 A1 | 8/2009 | Furcht et al. | |
| 2009/0233353 A1 | 9/2009 | Furcht et al. | |
| 2009/0233354 A1 | 9/2009 | Furcht et al. | |
| 2009/0304643 A1* | 12/2009 | Khurgel | A61K 47/48776 424/93.7 |
| 2010/0008890 A1 | 1/2010 | Mays et al. | |
| 2010/0150876 A1 | 6/2010 | Verfaillie et al. | |
| 2010/0285590 A1 | 11/2010 | Verfaillie et al. | |
| 2010/0310570 A1 | 12/2010 | Mays et al. | |
| 2011/0020292 A1 | 1/2011 | Van't Hof | |
| 2011/0020298 A1 | 1/2011 | Panitch et al. | |
| 2011/0171659 A1 | 7/2011 | Furcht et al. | |
| 2011/0177595 A1 | 7/2011 | Furcht et al. | |
| 2011/0206647 A1 | 8/2011 | Woda et al. | |
| 2011/0212069 A1 | 9/2011 | Hamilton et al. | |
| 2011/0213404 A1 | 9/2011 | Binkert | |
| 2011/0287539 A1 | 11/2011 | Pauwelyn et al. | |
| 2011/0293642 A1 | 12/2011 | Mays | |
| 2011/0305638 A1 | 12/2011 | Ting et al. | |
| 2011/0318313 A1 | 12/2011 | Cox, Jr. et al. | |
| 2012/0009674 A1 | 1/2012 | Mays | |
| 2012/0064047 A1 | 3/2012 | Verfaillie et al. | |
| 2012/0122215 A1 | 5/2012 | Edinger et al. | |
| 2012/0135043 A1 | 5/2012 | Maziarz et al. | |
| 2012/0308531 A1 | 12/2012 | Pinxteren et al. | |
| 2013/0129686 A1 | 5/2013 | Highfill et al. | |
| 2014/0024116 A1 | 1/2014 | Subramanian et al. | |
| 2014/0037596 A1 | 2/2014 | Woda et al. | |

FOREIGN PATENT DOCUMENTS

| | | |
|---|---|---|
| WO | 1998-43679 | 10/1998 |
| WO | WO 99/16863 | 4/1999 |
| WO | WO 99/35243 | 7/1999 |
| WO | WO 01/04268 | 1/2001 |
| WO | WO 01/08691 | 2/2001 |
| WO | WO 01/11011 * | 2/2001 |
| WO | WO 01/21766 | 3/2001 |
| WO | WO 01/21767 | 3/2001 |
| WO | WO 01/62901 | 8/2001 |
| WO | WO 02/08388 | 3/2002 |
| WO | WO 02/34890 | 5/2002 |
| WO | WO 07/067280 | 6/2007 |
| WO | WO 07/089798 | 8/2007 |
| WO | WO 09/092092 | 7/2009 |

OTHER PUBLICATIONS

Reyes et al., "Origin of endothelial progenitors in human postnatal bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc: 11:38-45 (2003).
Jiang et al., "Multipotent progenitor cells can be isolated from postnatal murine bone marrow, muscle, and brain" Exp. Hematol.: 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(-)CD38(-) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.; 28:1087-1095 (2002).
Verfaille, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR- cells in stroma-derived soluble factors, interleukin-3, and macrophage Inflammatory protein-1 alpha maintains not only myeloid but also lymphoid progenitors in a novel switch culture assay" Blood; 15:4516-4522 (1998).
Verfaille, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).

(56) References Cited

OTHER PUBLICATIONS

Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.: 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy: 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res: 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Natural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neurol.; 164:247-56 (2000).
Eglitis et al., "Hematopoietic cells differentiate into both microglia and macroglia in the brain of adult mice" Proc. Natl. Acad. Sci. USA: 94:4080-85 (1997).
Kopen et al., "Marrow stromal cells migrate throughout forebrain and cerebellum, and the differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Brazelton et al., "From marrow to brain: expression of neuronal phenotypes in adult mice" Science: 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253: 733-6 (1999).
Mezey et al., "Turning blood into brain: cells bearing neuronal antigens generated in vivo from bone marrow" Science: 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
Guan et al., "Pluripotency of spermatogonial stem cells from adult mouse testis"; Nature 24:1-5 (2006).
Anderson et al., "Transgenic Enrichment of Cardiomyocytes From Human Embryonic Stem Cells"; Molecular Therapy 15:2027-2036 (2007).
Dang et al., Efficiency of embryoid body formation and hematopoilic development from embryonic stem cells in different culture systems. Biotechnology and Bioengineering. (2002) vol. 78(4); pp. 442-453.
Kehoe et al. Scalable stirred-suspension bioreactor culture of human pluripotent stem cells. Tissue Engineering Part A (2009) vol. 16(2); pp. 405-421.
Youn et al. Large-scale expansion of mammary epithelial stem cell aggregates in suspension bioreactors. Biotechnology Progress (2005) vol. 21; pp. 984-993.
Subramanian, K., et al. Self-assembly of multipotent adult progenitor cells (MAPCs) and differentiation to the hepatic lineage. The 234th ACS National Meeting, Boston, MA; (2007); XP-002640240. p. 1.
Breyer, A., et al. Multipotent adult progenitor cell isolation and culture procedures. Exp. Hematology (2006) vol. 34; pp. 1596-1601.
Ulloa-Montoya, F., et al. Comparative transcriptome analysis of embryonic and adult stem cells with extended . . . Genome Biology (2007) vol. 8; pp. R163.1-R163.20.
Roobrouck, V.D., et al. Differentiation Potential of Human Postnatal Mesenchymal Stem Cells, Mesoangioblasts, and . . . Stem Cells (2011) vol. 29; pp. 871-882.
Cameron, C.M., et al. Improved Development of Human Embryonic Stem Cell-Derived Embryoid Bodies by Stirred Vessel Cultivation. Biotech. and Bioeng. (2006); vol. 94, No. 5; pp. 938-948.
Fok, E.Y.L., et al. Shear-Controlled Single-Step Mouse Embryonic Stem Cell Expansion and Embryoid Body-Based Differentiation. Stem Cells (2005); vol. 23, No. 9, pp. 1333-1342.
Sargent, C.Y., et al. Hydrodynamic Modulation of Embryonic Stem Cell Differentiation by Rotary Orbital Suspension Culture. Biotech. and Bioeng. (2010); vol. 105, No. 3; pp. 611-628.
Steiner, D., et al. Derivation, Propagation and Controlled Differentiation of Human Embryonic Stem Cells in Suspension. Nature Biotech. (2010); vol. 28, No. 4; pp. 361-364.
Subramanian, K., et al. Scalable Expansion of Multipotent Adult Progenitor Cells as Three-Dimensional Cell Aggregates. Biotech. and Bioeng. (2011); vol. 108, No. 2: pp. 364-375.
Liedtke, S., et al. Oct4 expression revisited: potential pitfalls for data misinterpretation in stem cell research. Biol. Chem. (2008) vol. 389: pp. 845-850.
Kolf, C.M., et al. Review Mesenchymal stromal cells: Biology of adult mesenchymal stem cells: regulation of niche, self-renewal and differentiation. Arthritis Research & Therapy (2007) vol. 9:204; pp. 1-10.
Herzog, E.L. et al., Plasticity of marrow-derived stem cells. Blood, (2003), vol. 102, No. 10, pp. 3483-3493.
U.S. Patent and Trademark Office, Office Action and 892 dated Jul. 28, 2015, in related U.S. Appl. No. 13/957,987.
Kraft, H.J., et al. Oct-4 Regulates Alternative Platelet-derived Growth Factor α Receptor Gene Promoter in Human Embryonal Carcinoma Cells. J Biol Chem; 1996; vol. 271, No. 22; pp. 12873-12878.
Zheng, X-S., et al. "Suspending Instability of Neural Stem Cell Clusters and Its Solution"; Chinese J. Biomed. Eng.; (2006) vol. 25, No. 5, pp. 607-612.
Ezashi, et al., "Low O2 tensions and the prevention of differentiation of hES cells", PNAS USA, 102:4763-8, Mar. 29, 2005.
Roche et al., Oct-4, Rex-1, and Gata-4 Expression in Human MSC Increase the Differentiation Efficiency But Not hTERT Expression, Journal of Cellular Biochemistry 101 : 271-280 (2007).
Wu et al., Generation of Pancreatic β Cells From Mesenchymal Stem Cells to Treat Type 1 Diabetes, OA Stem Cells, Mar. 22, 2014 ; 2 (1) : 5.

(56) References Cited

OTHER PUBLICATIONS

Guo et al., Differentiation of Mesenchymal Stem Cells Into Dopaminergic Neruon-like Cells in Vitro, Biomedical and Environmental Sciences, 18, 36-42 (2005).
Piccinato et al., High OCT4 and Low p16INK4A Expressions Determine in Vitro Lifespan of Mesenchymal Stem Cells, Stem Cells International, vol. 2015, Article ID 369828, 11 pages.
U.S. Appl. No. 11/808,933, filed Jun. 13, 2007, High Oct3/4 MAPCs and Methods Therefor.

* cited by examiner

FIG. 5
- LOW OCT4 MAPC AGGREGATES WERE FORMED FROM 8000 CELLS AND TOOK 7 DAYS TO FORM.
- SIZE: ~150-200 μm
- DIFFERENTIATED SPONTANEOUSLY TO DIFFERENT CELL TYPES
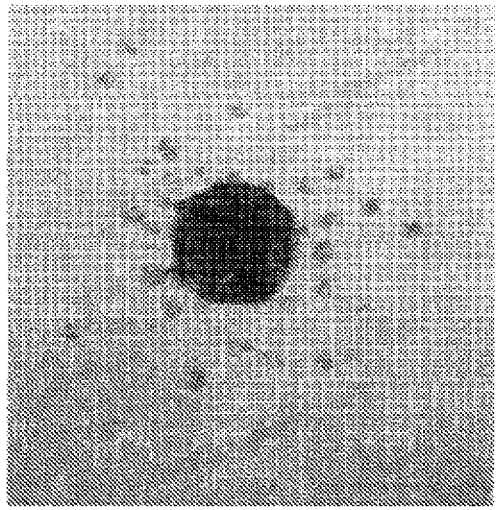
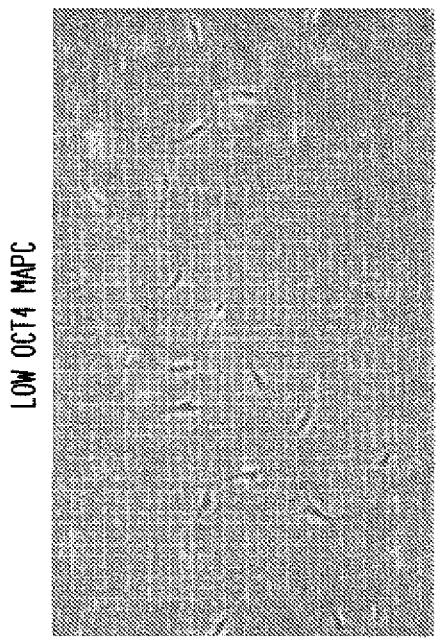
LOW OCT4 MAPC
MAPC MEDIA, 5% O$_2$
LOW OCT4 MAPC AGGREGATE
DIFF BASAL MEDIA, 21% O$_2$

STEM CELL AGGREGATES AND METHODS FOR MAKING AND USING

RELATED APPLICATIONS

The present application claims priority to U.S. Provisional Application No. 61/022,121, filed Jan. 18, 2008, which is incorporated herein by reference.

FIELD OF THE INVENTION

The invention is directed to compositions of cell aggregates and methods for making and using the cell aggregates where the aggregates comprise cells that are not embryonic stem cells but can differentiate into cell types of at least two of ectodermal, endodermal, and mesodermal embryonic germ layers, e.g., stem cells.

BACKGROUND OF THE INVENTION

Stem Cells

Stem cells are characterized in that they are capable of self renewal (cell division without differentiation) and also of producing progeny that are more differentiated. The quintessential stem cell historically is the embryonic stem (ES) cell. The ES cell has unlimited self-renewal. ES cells are derived from the inner cell mass of the blastocyst or primordial germ cells from a post-implantation embryo (embryonal germ cells or EG cells). ES and EG cells have been derived, among others, from mouse, non-human primates and humans. When introduced into blastocysts, ES cells can contribute to all tissues. A drawback to ES cell therapy is that when transplanted in post-natal animals, ES and EG cells generate teratomas.

ES (and EG) cells can be identified by positive staining with antibodies to SSEA1 (mouse) and SSEA4 (human). At the molecular level, ES and EG cells express a number of transcription factors specific for these undifferentiated cells. These include oct3/4 and rex-1. Also found are the LIF-R (in mouse) and the transcription factors sox-2 and rox-1. Rox-1 and sox-2 are also expressed in non-ES cells. A hallmark of ES cells is telomerase enzyme activity, which provides these cells with an unlimited self-renewal potential in vitro. See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701, 6,500,668; 6,703,279; 6,875,607; 7,029,913; 7,112,437; 7,145,057; 7,153,684; and 7,294,508, each of which is incorporated by reference for teaching ES cells and methods of making them. ES cells have been grown in aggregate form. They are able to form embryoid bodies when grown without attachment to a substrate.

Oct3/4 (oct3 in humans) is a transcription factor expressed in the pregastrulation embryo, early cleavage stage embryo, cells of the inner cell mass of the blastocyst, and in embryonic carcinoma (EC) cells (Nichols et al., *Cell* 95:379-91 (1998)), and is down-regulated when cells are induced to differentiate. Expression of oct3/4 plays an important role in determining early steps in embryogenesis and differentiation. Oct3/4, in combination with rox-1, causes transcriptional activation of the Zn-finger protein rex-1, also required for maintaining undifferentiated ES cells (Rosfjord and Rizzino, *Biochem Biophys Res Commun* 203:1795-802 (1997); Ben-Shushan et al., *Mol Cell Biol* 18:1866-78 (1998)). In addition, sox-2, expressed in ESC/EC, but also in other more differentiated cells, is needed together with oct3/4 to retain the undifferentiated state (Uwanogho et al., *Mech Dev* 49:23-36 (1995)). Maintenance of murine ES cells and primordial germ cells requires the presence of LIF. The oct3/4 gene is transcribed into at least two splice variants in humans, oct3A and oct3B. The oct3B splice variant is found in many differentiated cells whereas the oct3A splice variant (also previously designated oct3/4) is reported to be specific for the undifferentiated ES cell. See Shimozaki et al. *Development* 130:2505-12 (2003).

SUMMARY OF THE INVENTION

1. The invention provides a composition comprising an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

2. The invention further provides a composition comprising an aggregate of cells in cell culture, wherein said aggregate of cells comprises cells that are not embryonic stem cells, embryonic germ cells, or germ cells and can differentiate into cell types of at least two of the endodermal, ectodermal and mesodermal embryonic lineages.

3. The invention further provides a pharmaceutical composition comprising a pharmaceutically-acceptable carrier and an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

4. The invention further provides a composition comprising cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

5. The invention further provides a composition comprising, in cell culture, cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

6. The invention further provides a pharmaceutical composition comprising a pharmaceutically-acceptable carrier and cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

7. The invention further provides a composition comprising a differentiated cell produced by exposing an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages, to conditions producing said differentiated cell.

8. The invention further provides a composition comprising, in cell culture, a differentiated cell produced by exposing an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages, to conditions producing said differentiated cell.

9. The invention further provides a pharmaceutical composition comprising a pharmaceutically-acceptable carrier and a differentiated cell, said differentiated cell produced by exposing an aggregate of cells, wherein said aggregate of cells comprises cells that are not embryonic stem cells, embryonic germ cells, or germ cells and that can differentiate into cell types of at least two of the endodermal, ectodermal and mesodermal embryonic lineages, to conditions producing said differentiated cell.

10. The invention further provides a composition comprising a differentiated cell produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

11. The invention further provides a composition, comprising, in cell culture, a differentiated cell produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

12. The invention further provides a pharmaceutical composition comprising a pharmaceutically-acceptable carrier and a differentiated cell produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

13. The invention further provides a method for making an aggregate of cells, said method comprising exposing cells that are not embryonic stem cells, embryonic germ cells, or germ cells and can differentiate into cell types of at least two of the endodermal, ectodermal and mesodermal embryonic lineages to conditions under which said cells aggregate.

14. The invention further provides a method for making an aggregate of cells in cell culture, said method comprising exposing cells, in cell culture, to conditions under which said cells aggregate, wherein said cells from which the aggregate is made are not embryonic stem cells, embryonic germ cells, or germ cells and can differentiate into cell types of at least two of the endodermal, ectodermal and mesodermal embryonic lineages.

15. The invention further provides a method for making a pharmaceutical composition, said method comprising admixing a pharmaceutically-acceptable carrier with an aggregate of cells, said aggregate of cells comprising cells that are not embryonic stem cells, embryonic germ cells, or germ cells and can differentiate into cell types of at least two of the endodermal, ectodermal and mesodermal embryonic lineages.

16. The invention further provides a method for making cells derived from an aggregate of cells, said method comprising dis-aggregating cells in an aggregate of cells, said aggregate of cells comprising cells that are not embryonic stem cells, embryonic germ cells, or germ cells and can differentiate into cell types of at least two of the endodermal, ectodermal and mesodermal embryonic lineages.

17. The invention further provides a method for making a cell culture composition, said method comprising introducing, into a culture medium, cells derived from an aggregate of cells, wherein said aggregate of cells comprises cells that are not embryonic stem cells, embryonic germ cells, or germ cells and can differentiate into cell types of at least two of the endodermal, ectodermal, and mesodermal embryonic lineages.

18. The invention further provides a method for making a pharmaceutical composition, said method comprising admixing a pharmaceutically-acceptable carrier with cells derived from an aggregate of cells, wherein said aggregate of cells comprises cells that are not embryonic stem cells, embryonic germ cells, or germ cells and can differentiate into cell types of at least two of the endodermal, ectodermal, and mesodermal embryonic lineages.

19. The invention further provides a method for making a differentiated cell, said method comprising exposing an aggregate of cells, wherein said aggregate of cells comprises cells that are not embryonic stem cells, embryonic germ cells, or germ cells and can differentiate into cell types of at feast two of the endodermal, ectodermal, and mesodermal embryonic lineages, to conditions producing said differentiated cell.

20. The invention further provides a method for making a differentiated cell, said method comprising exposing an aggregate of cells, in cell culture, to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

21. The invention further provides a method for making a cell culture composition, said method comprising combining a differentiated cell with a cell culture medium, said differentiated cell having been produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal, and mesodermal embryonic lineages.

22. The invention further provides a method for making a pharmaceutical composition, said method comprising admixing a pharmaceutically-acceptable carrier with a differentiated cell produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

23. The invention further provides a method for making a differentiated cell, said method comprising exposing a cell derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal, and mesodermal embryonic lineages.

24. The invention further provides a method for making a differentiated cell, said method comprising exposing, in cell culture, cells derived from an aggregate of cells to conditions producing said differentiated cell, wherein said aggregate of cells comprises cells are not embryonic stem cells, embryonic germ cells, or germ cells and can differentiate into cell types of at least two of the endodermal, ectodermal and mesodermal embryonic lineages.

25. The invention further provides a method for making a cell culture composition, said method comprising combining a differentiated cell with a cell culture medium, said differentiated cell having been produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal, and mesodermal embryonic lineages.

26. The invention further provides a method for making a pharmaceutical composition, said method comprising admixing a differentiated cell with a pharmaceutically-acceptable carrier, said cell having been produced by exposing cells derived from an aggregate of cells to conditions effective to achieve the differentiated cell phenotype, wherein said aggregate of cells comprises cells that are not embryonic stem cells, embryonic germ cells, or germ cells and can differentiate into cell types of at least two of the endodermal, ectodermal, and mesodermal embryonic lineages.

27. The invention further provides a method comprising administering to a subject an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

28. The invention further provides a method comprising administering to a subject a pharmaceutical composition comprising a pharmaceutically-acceptable carrier and an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

29. The invention further provides a method comprising administering to a subject cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

30. The invention further provides a method comprising administering to a subject a pharmaceutical composition comprising a pharmaceutically-acceptable carrier and cells derived from an aggregate of cells, wherein said aggregate of cells comprises cells that are not embryonic stem cells, embryonic germ cells, or germ cells and can differentiate into cell types of at least two of the endodermal, ectodermal, and mesodermal embryonic lineages.

31. The invention further provides a method comprising administering to a subject a differentiated cell produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

32. The invention further provides a method comprising administering to a subject a pharmaceutical composition comprising a pharmaceutically-acceptable carrier and a differentiated cell, the differentiated cell produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal, and mesodermal embryonic lineages.

33. The invention further provides a method comprising administering to a subject a differentiated cell produced by exposing cells derived from an aggregate of cells to conditions producing said differentiated cell, wherein said aggregate of cells comprises cells that are not embryonic stem cells, embryonic germ cells, or germ cells and that can differentiate into cell types of at least two of the endodermal, ectodermal and mesodermal embryonic lineages.

34. The invention further provides a method comprising administering to a subject a pharmaceutical composition comprising a pharmaceutically-acceptable carrier and a differentiated cell, the differentiated cell produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal, and mesodermal embryonic lineages.

35. The invention further provides a method of identifying an active agent, said method comprising contacting an aggregate of cells with an agent, wherein said aggregate of cells comprises cells that are not embryonic stem cells, embryonic germ cells, or germ cells and can differentiate into cell types of at least two of the endodermal, ectodermal and mesodermal embryonic lineages, and detecting the effect of the agent on said aggregate of cells.

36. The invention further provides a method of identifying an active agent, said method comprising contacting an aggregate of cells with an agent in cell culture, wherein said aggregate of cells comprises cells that are not embryonic stem cells, embryonic germ cells, or germ cells and can differentiate into cell types of at least two of the endodermal, ectodermal and mesodermal embryonic lineages, and detecting the effect of the agent on said aggregate of cells.

37. The invention further provides a method of identifying an active agent, said method comprising contacting cells derived from an aggregate of cells with an agent, wherein said aggregate of cells comprises cells that are not embryonic stem cells, embryonic germ cells, or germ cells and can differentiate into cell types of at least two of the endodermal, ectodermal and mesodermal embryonic lineages, and detecting the effect of the agent on said cells derived from said aggregate of cells.

38. The invention further provides a method of identifying an active agent, said method comprising contacting, in cell culture, cells derived from an aggregate of cells with an agent, wherein said aggregate of cells comprises cells that are not embryonic stem cells, embryonic germ cells, or germ cells and can differentiate into cell types of at least two of the endodermal, ectodermal and mesodermal embryonic lineages, and detecting the effect of the agent on said cells derived from said aggregate of cells.

39. The invention further provides a method of treating a disorder in a subject in need of treatment, said method comprising administering a therapeutically effective amount of an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

40. The invention further provides a method of treating a disorder in a subject in need of treatment, said method comprising administering a therapeutically effective amount of a pharmaceutical composition comprising a pharmaceutically-acceptable carrier and an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

41. The invention further provides a method of treating a disorder in a subject in need of treatment, said method comprising administering a therapeutically effective amount of cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

42. The invention further provides a method of treating a disorder in a subject in need of treatment, said method comprising administering a therapeutically effective amount of a pharmaceutical composition comprised of a pharmaceutically-acceptable carrier and cells derived from an aggregate of cells, wherein said aggregate of cells comprises cells that are not embryonic stem cells, embryonic germ cells, or germ cells and can differentiate into cell types of at least two of the endodermal, ectodermal and mesodermal embryonic lineages.

43. The invention further provides a method of treating a disorder in a subject in need of treatment, said method comprising administering a therapeutically effective amount of a differentiated cell produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

44. The invention further provides a method of treating a disorder in a subject in need of treatment, said method comprising administering a therapeutically effective amount of a pharmaceutical composition comprising a pharmaceutically-acceptable carrier and a differentiated cell, said differentiated cell produced by exposing an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

45. The invention further provides a method of treating a disorder in a subject in need of treatment, said method comprising administering a therapeutically effective amount of a differentiated cell produced by exposing cells derived from an aggregate of cells to conditions producing said differentiated cell, wherein said aggregate of cells comprises cells that are not embryonic stem cells, embryonic germ cells, or germ cells and can differentiate into cell types of at least two of the endodermal, ectodermal and mesodermal embryonic lineages.

46. The invention further provides a method of treating a disorder in a subject in need of treatment, said method comprising administering a therapeutically effective amount of a pharmaceutical composition comprising a pharmaceutically-acceptable carrier and a differentiated cell produced by exposing cells derived from an aggregate of cells to conditions producing said differentiated cell, wherein said aggregate of cells comprises cells that not embryonic stem cells, embryonic germ cells, or germ cells and can differentiate into cell types of at least two of the endodermal, ectodermal and mesodermal embryonic lineages.

47. The invention further provides the compositions herein, wherein cells in the aggregate and cells derived from the aggregate express one or more of oct3/4, telomerase, rex-1, rox-1, nanog, GATA6 and sox-2.

48. The invention further provides the compositions herein, wherein cells in the aggregate and cells derived from the aggregate can differentiate into cell types of all three of the endodermal, ectodermal, and mesodermal embryonic lineages.

49. The invention further provides the compositions herein, wherein the differentiated cell, produced by differentiating the aggregate or cells derived from the aggregate, expresses one or more of endodermal, ectodermal, and mesodermal differentiation markers.

50. The invention further provides the compositions herein, wherein the differentiated cell, produced by differentiating the aggregate or cells derived from the aggregate, expresses endodermal and ectodermal differentiation markers.

51. The invention further provides the compositions herein, wherein the differentiated cell, produced by differentiating the aggregate or cells derived from the aggregate, expresses ectodermal and mesodermal differentiation markers.

52. The invention further provides the compositions herein, wherein the differentiated cell, produced by differentiating the aggregate or cells derived from the aggregate, expresses endodermal and mesodermal differentiation markers.

53. The invention further provides the compositions herein, wherein the differentiated cell, produced by differentiating the aggregate or cells derived from the aggregate, expresses an endodermal differentiation marker.

54. The invention further provides the compositions herein, wherein the differentiated cell, produced by differentiating the aggregate or cells derived from the aggregate, expresses an ectodermal differentiation marker.

55. The invention further provides the compositions herein, wherein the differentiated cell, produced by differentiating the aggregate or cells derived from the aggregate, expresses a mesodermal differentiation marker.

56. The invention further provides the compositions herein, wherein the differentiated cell phenotype, produced by differentiating the aggregate or cells derived from the aggregate, is characteristic of cells selected from the group consisting of hepatocytes, beta islet cells, neurons, osteoblasts, astrocytes, oligodendrocytes, cartilage, bone, muscle, connective tissue, mesangioblasts, hematopoietic stem cells, lymphocytes, reticulocytes, myeloid cells, pulmonary epithelia and skin.

57. The invention further provides the compositions herein, wherein the aggregate contains about 10 cells to about 50,000 cells or more.

58. The invention further provides the compositions herein, wherein the aggregate contains about 1000 cells to about 5000 cells.

59. The invention further provides the compositions herein, wherein cells are aggregated by the hanging drop method or forced aggregation method.

60. The invention further provides the compositions herein, wherein the differentiated cell phenotype is selected from the group consisting of osteoblast, chondrocyte, bone, adipocyte, cartilage, fibroblast, marrow stroma, skeletal muscle, smooth muscle, cardiac muscle, ocular, endothelial, epithelial, hepatic, pancreatic, hematopoietic, glial, neuronal and oligodendrocyte cell type.

61. The invention further provides the compositions herein, wherein the differentiated cell is definitive endoderm.

62. The invention further provides the compositions herein, wherein the differentiated cell is ventral foregut endoderm.

63. The invention further provides the compositions herein, wherein the differentiated cell is a bi-potential hepatic progenitor.

64. The invention further provides the compositions herein, wherein the differentiated cell is a hepatocyte-like cell.

65. The invention further provides the methods herein, wherein cells in the aggregate or cells derived from the aggregate express one or more of oct3/4, telomerase, rex-1, rax-1, nanog, GATA6 and sox-2.

66. The invention further provides the methods herein, wherein cells in the aggregate or cells derived from the aggregate can differentiate into cell types of all three of the endodermal, ectodermal and mesodermal embryonic lineages.

67. The invention further provides the methods herein, wherein the differentiated cell, produced by differentiating the aggregate or cells derived from the aggregate, expresses one or more of endodermal, ectodermal and mesodermal differentiation markers.

68. The invention further provides the methods herein, wherein the differentiated cell, produced by differentiating the aggregate or cells derived from the aggregate, expresses endodermal and ectodermal differentiation markers.

69. The invention further provides the methods herein, wherein the differentiated cell, produced by differentiating the aggregate or cells derived from the aggregate, expresses ectodermal and mesodermal differentiation markers.

70. The invention further provides the methods herein, wherein the differentiated cell, produced by differentiating the aggregate or cells derived from the aggregate, expresses endodermal and mesodermal differentiation markers.

71. The invention further provides the methods herein, wherein the differentiated cell, produced by differentiating the aggregate or cells derived from the aggregate, expresses an endodermal differentiation marker.

72. The invention further provides the methods herein, wherein the differentiated cell, produced by differentiating the aggregate or cells derived from the aggregate, expresses an ectodermal differentiation marker.

73. The invention further provides the methods herein, wherein the differentiated cell, produced by differentiating the aggregate or cells derived from the aggregate, expresses a mesodermal differentiation marker.

74. The invention further provides the methods herein, wherein the differentiated cell phenotype is characteristic of cells selected from the group consisting of hepatocytes, beta islet cells, neurons, osteoblasts, astrocytes, oligodendrocytes, cartilage, bone, muscle, connective tissue, mesangioblasts, hematopoietic stem cells, lymphocytes, reticulocytes, myeloid cells, pulmonary epithelia and skin.

75. The invention further provides the methods herein, wherein the aggregate contains about 10 cells to about 50,000 cells or more.

76. The invention further provides the methods herein, wherein the aggregate contains about 1000 cells to about 5000 cells.

77. The invention further provides the methods herein, wherein cells are aggregated by the hanging drop method or forced aggregation method.

78. The invention further provides the methods herein, wherein the disorder is a liver disease or disorder, GVHD, myocardial infarction, congestive heart failure, diabetes, hematopoietic transplant, traumatic brain injury, spinal cord injury or stroke.

79. The invention further provides the methods herein, wherein the disorder involves damaged tissue and the tissue is one or more of cardiac, neuronal, ocular, cartilage, bone, skeletal muscle, smooth muscle, bone marrow, spleen, liver, lung, brain, immune system, connective, blood vessel, pancreas, CNS, PNS and kidney tissue.

80. The invention further provides the methods herein, wherein the differentiated cell phenotype is selected from the group consisting of osteoblast, chondrocyte, bone, adipocyte, cartilage, fibroblast, marrow stroma, skeletal muscle, smooth muscle, cardiac muscle, ocular, endothelial, epithelial, hepatic, pancreatic, hematopoietic, glial, neuronal and oligodendrocyte cell type.

81. The invention further provides the methods herein, wherein the differentiated cell is definitive endoderm.

82. The invention further provides the methods herein, wherein the differentiated cell is ventral foregut endoderm.

83. The invention further provides the methods herein, wherein the differentiated cell is a bi-potential hepatic progenitor.

84. The invention further provides the methods herein, wherein the differentiated cell is a hepatocyte-like cell.

In the above statements of the invention, cells derived from the aggregate can retain the differentiation capacity of the aggregated cells.

BRIEF DESCRIPTION OF THE FIGURES

FIG. 5 shows low oct3/4 MAPC aggregates formed from low oct3/4 MAPCs in 2D culture in MAPC medium and 5% oxygen in 7 days. Upon spontaneous differentiation in differentiation basal media and 21% oxygen, aggregates differentiated to cells that appeared like adipocytes and fibroblasts by morphology.

DETAILED DESCRIPTION OF THE INVENTION

Definitions

Figure 1:
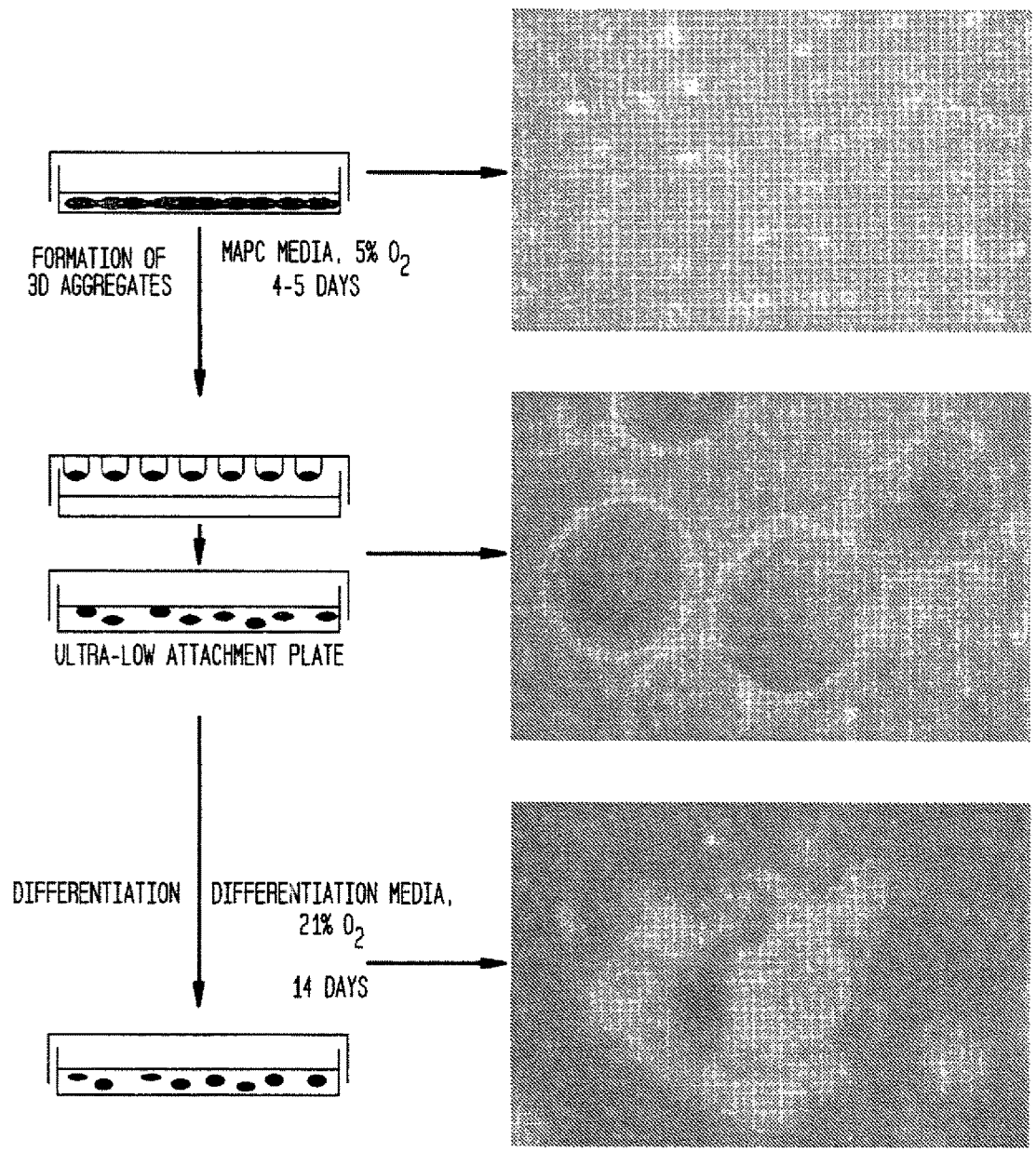
FIG. 1 shows the hanging drop method for forming aggregates from rat MAPCs in monolayer (2D) culture and subsequent differentiation. After 4-5 days of aggregate formation in the hanging drop in MAPC media and 5% oxygen, cell aggregates are transferred to the ultra-low attachment plate for differentiation in corresponding differentiation media. The right panel illustrates the morphology of the cells in 2D monolayer, undifferentiated cell aggregates, and then differentiated cell aggregates.
Figure 2:
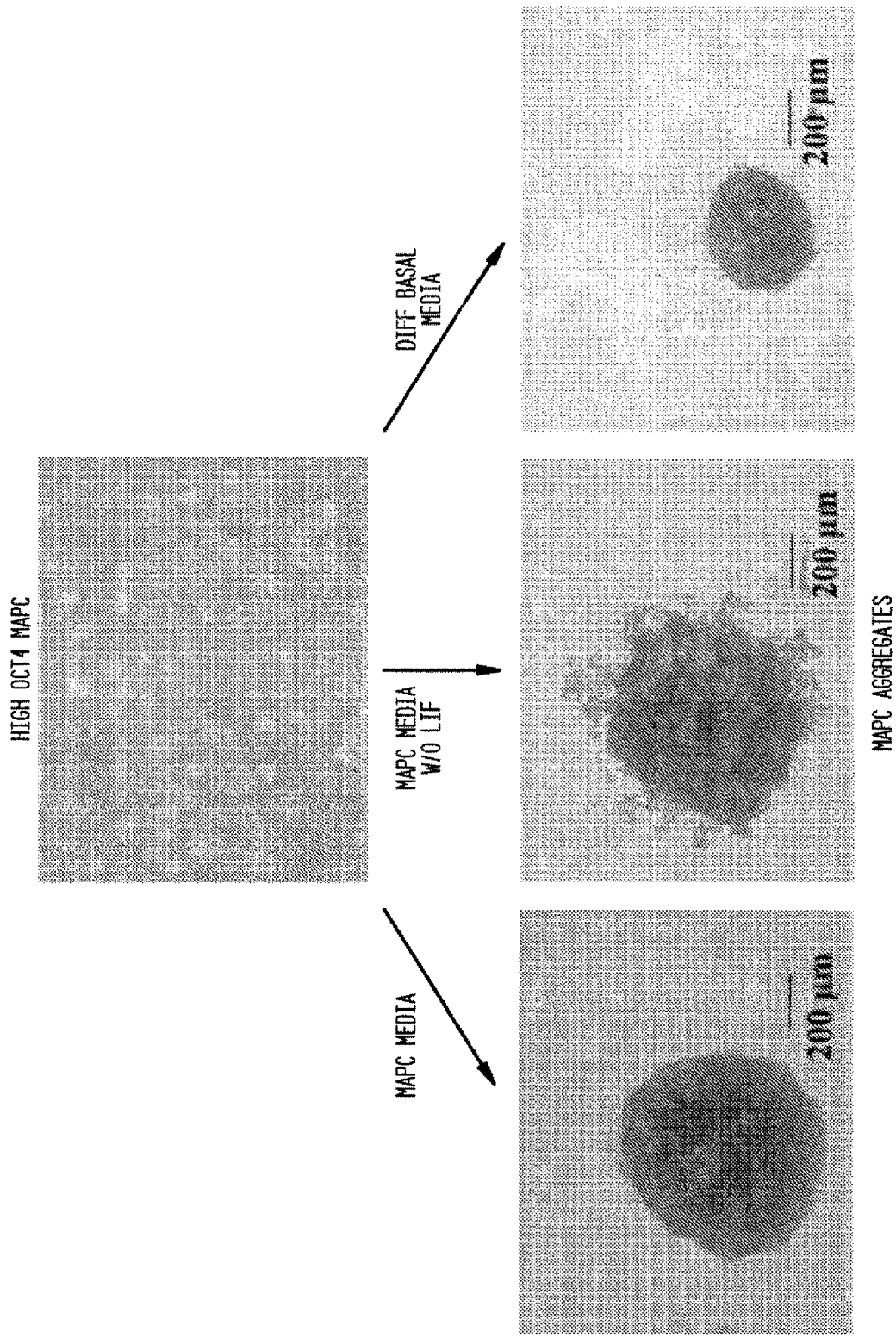
FIG. 2 shows aggregates formed from rat MAPC under different media conditions. Under optimum MAPC media conditions, the aggregates grow up into spherical clusters with well defined boundary. Withdrawal of LIF from MAPC media induces formation of aggregates with irregular boundary corresponding to early signs of differentiation. In differentiation basal media, the cell aggregates are much smaller due to non-optimal growth conditions.
Figure 3:
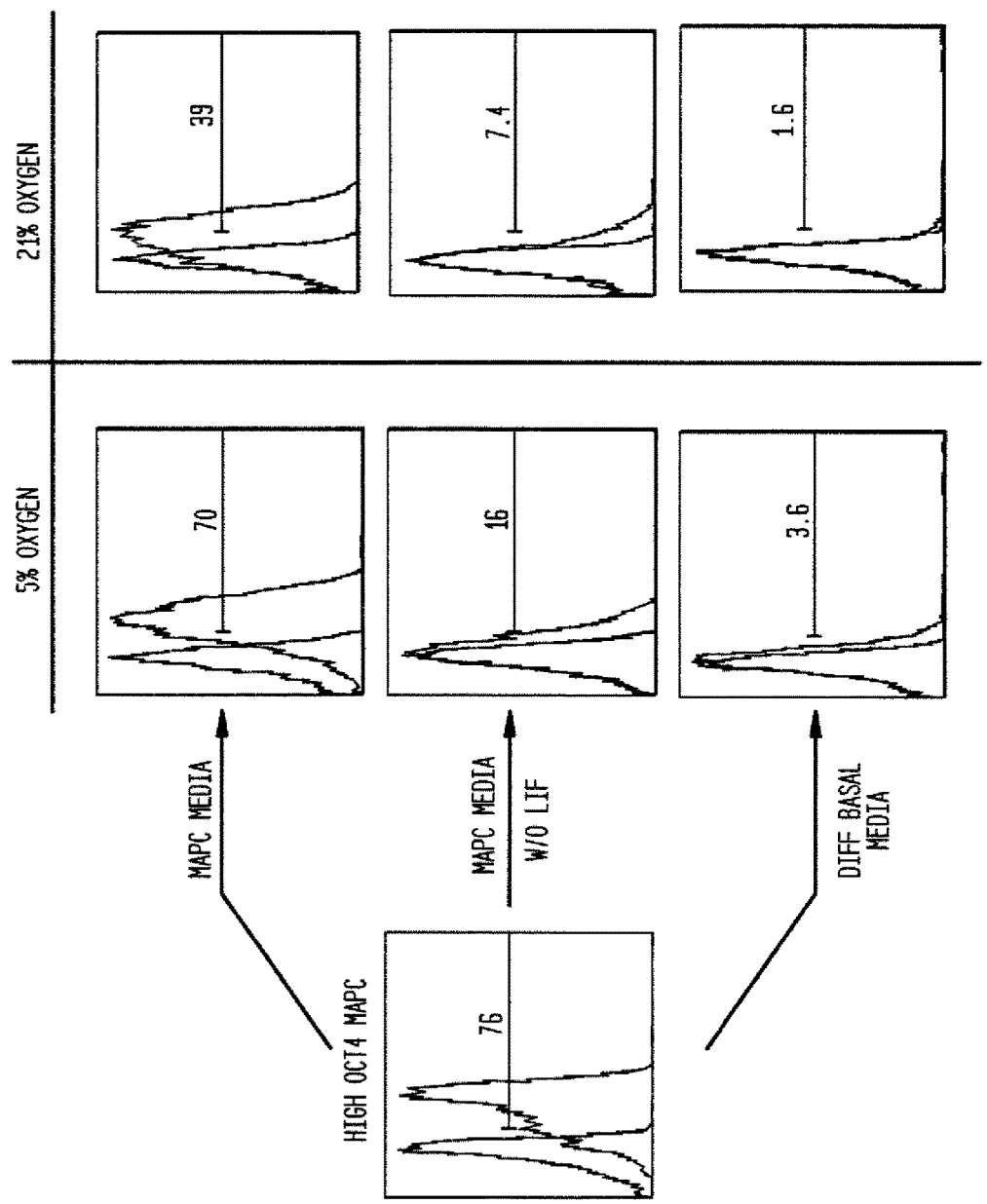
FIG. 3 shows the percentage of cells expressing oct3/4 (transcription factor associated with the undifferentiated status of MAPCs). Out of the 76% of cells that expressed oct3/4 in 2D monolayer, 70% still retained the expression of oct3/4 in the MAPC aggregates when they were formed in MPAC media and 5% oxygen. Other conditions were different media compositions:—MAPC media without LIF, differentiation basal media, and choice of oxygen levels— 5% (hypoxic) or 21% (normoxic).
Figure 4:
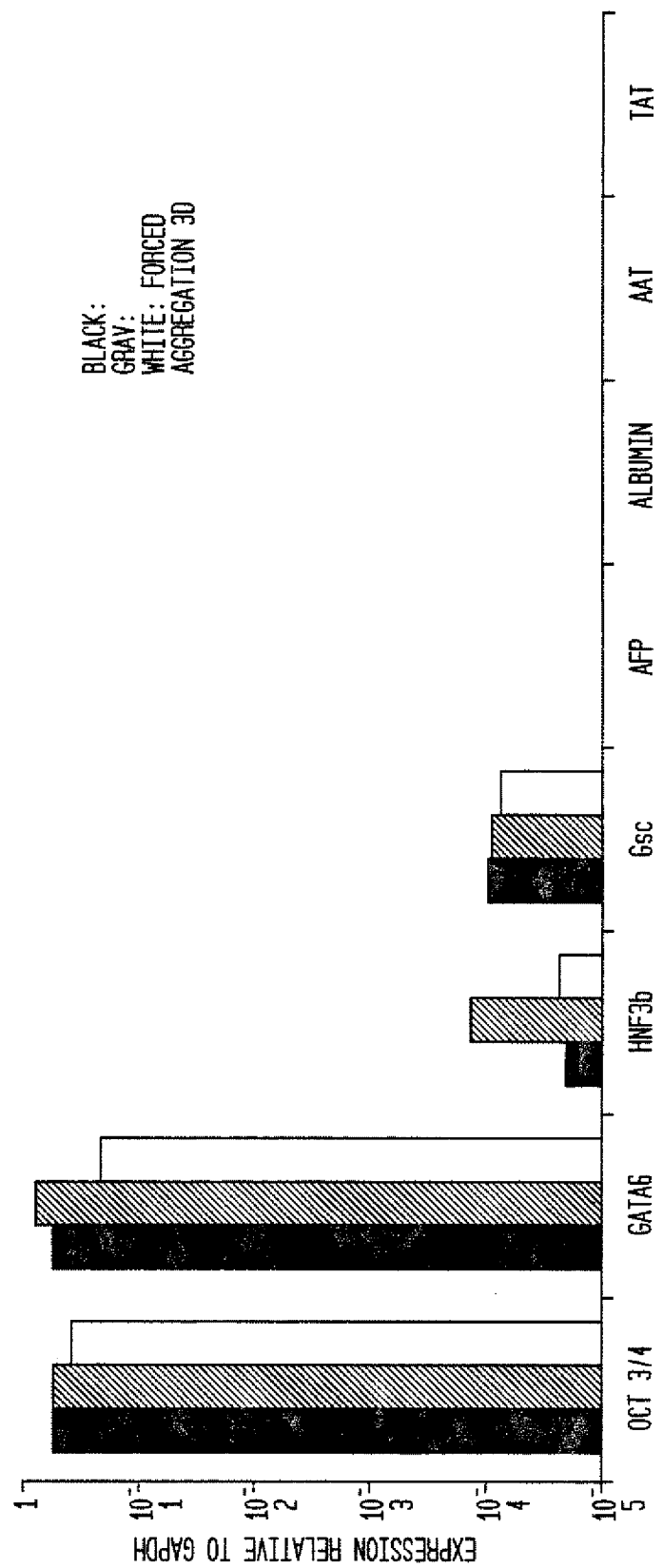
FIG. 4 shows a QRT-PCR expression profile for several differentiation markers in MAPC 2D and 3D cultures formed by the hanging drop method and forced aggregation method. The expression of oct3/4 and GATA6 are both comparable between 2D MAPCs and 3D MAPC aggregates irrespective of the method of formation. There is little expression of early endoderm markers HNF3b and Goosecoid (Gsc) and no expression of mature endoderm markers like AFP, albumin, Alpha-1-Antitrypsin (AAT) and Tyrosine amino transferase (TAT) in 3D MAPC aggregates similar to MAPCs 2D.
Figure 6:
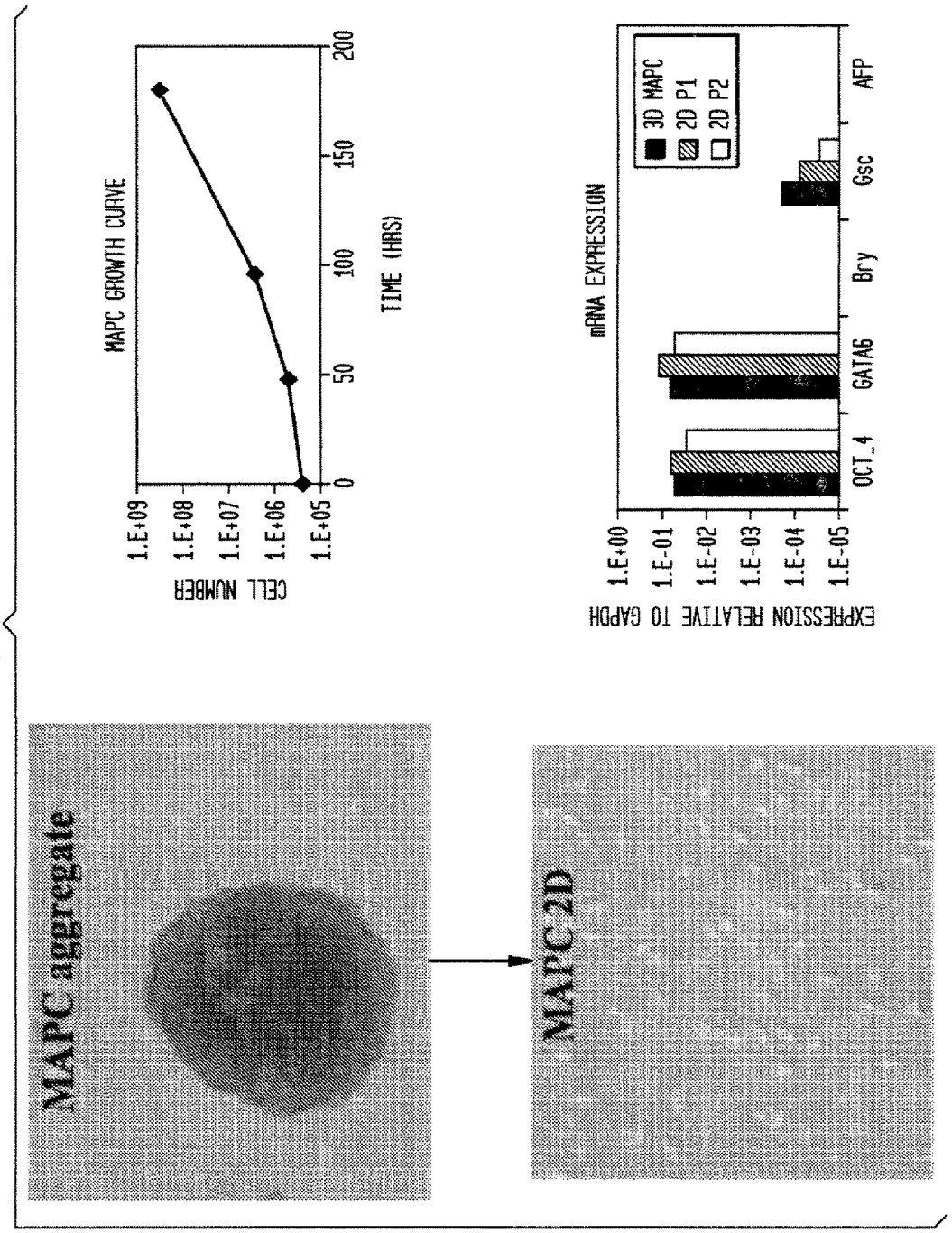
FIG. 6 shows high oct3/4 MAPC trypsinized and replated onto fibronectin-coated dishes in MAPC medium and 5% oxygen. The morphology of cells are typical of MAPCs, they are capable of undergoing expansion illustrated by the increase in cell number with time and retain the expression of MAPC markers oct3/4 and GATA6 at passage 1 (2D P2) and passage 2 (2D P2) after replating at levels expressed by MAPCs aggregates they came from. There is little or no expression of early differentiated markers like Goosecoid (Gsc) or Brachyury (Bry) and no expression of more mature marker like Alpha-fetoprotein (AFP).
Figure 7:
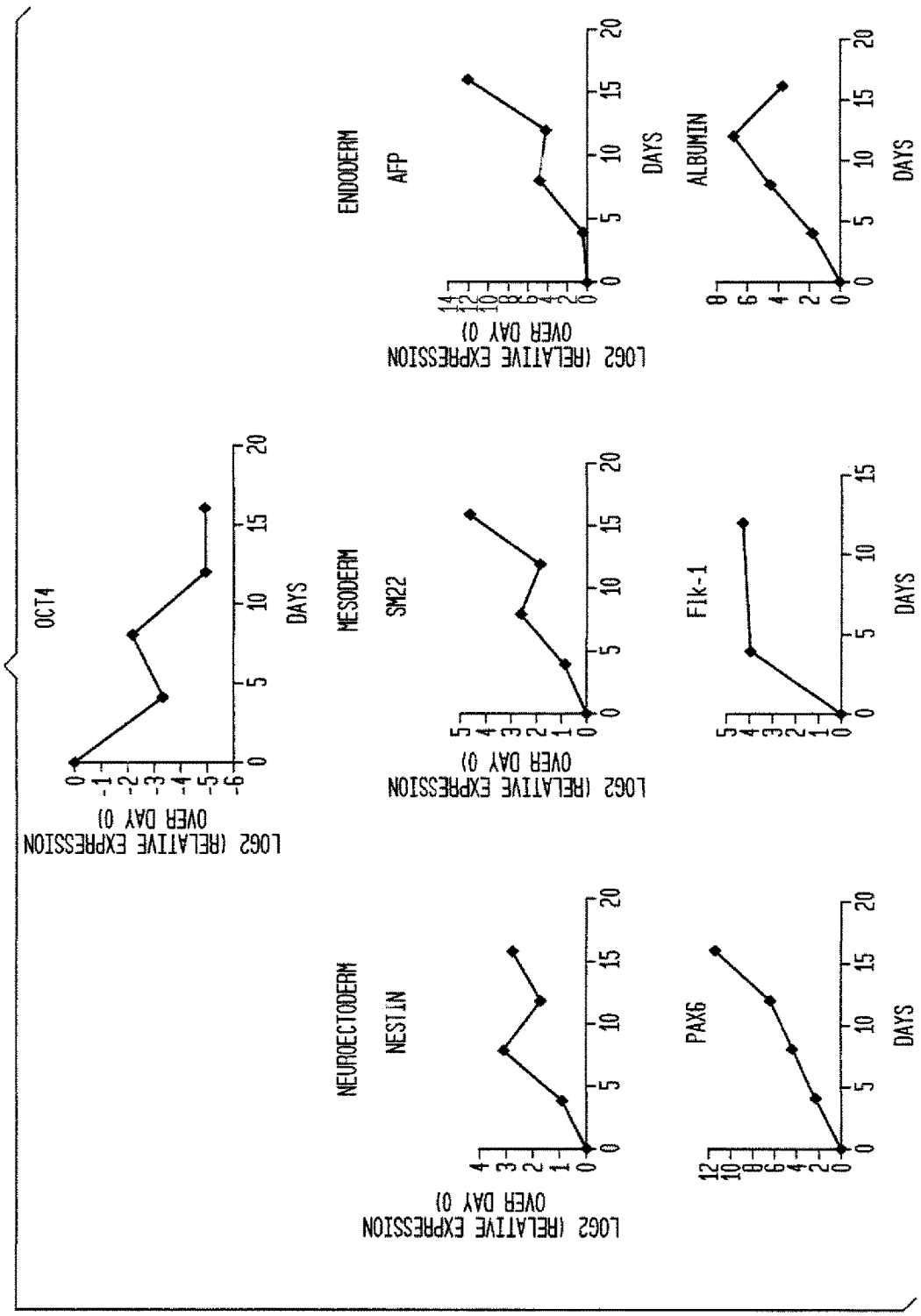
FIG. 7 shows spontaneous multi-lineage differentiation of MAPC aggregates in differentiation basal medium with 2% serum. The levels of oct3/4 goes down corresponding to differentiation and increase in expression of markers of the three germ layers are observed-Nestin, Pax6 (neuroectoderm), SM22, Flk-1 (mesoderm), AFP, Albumin (endoderm).
Figure 8:
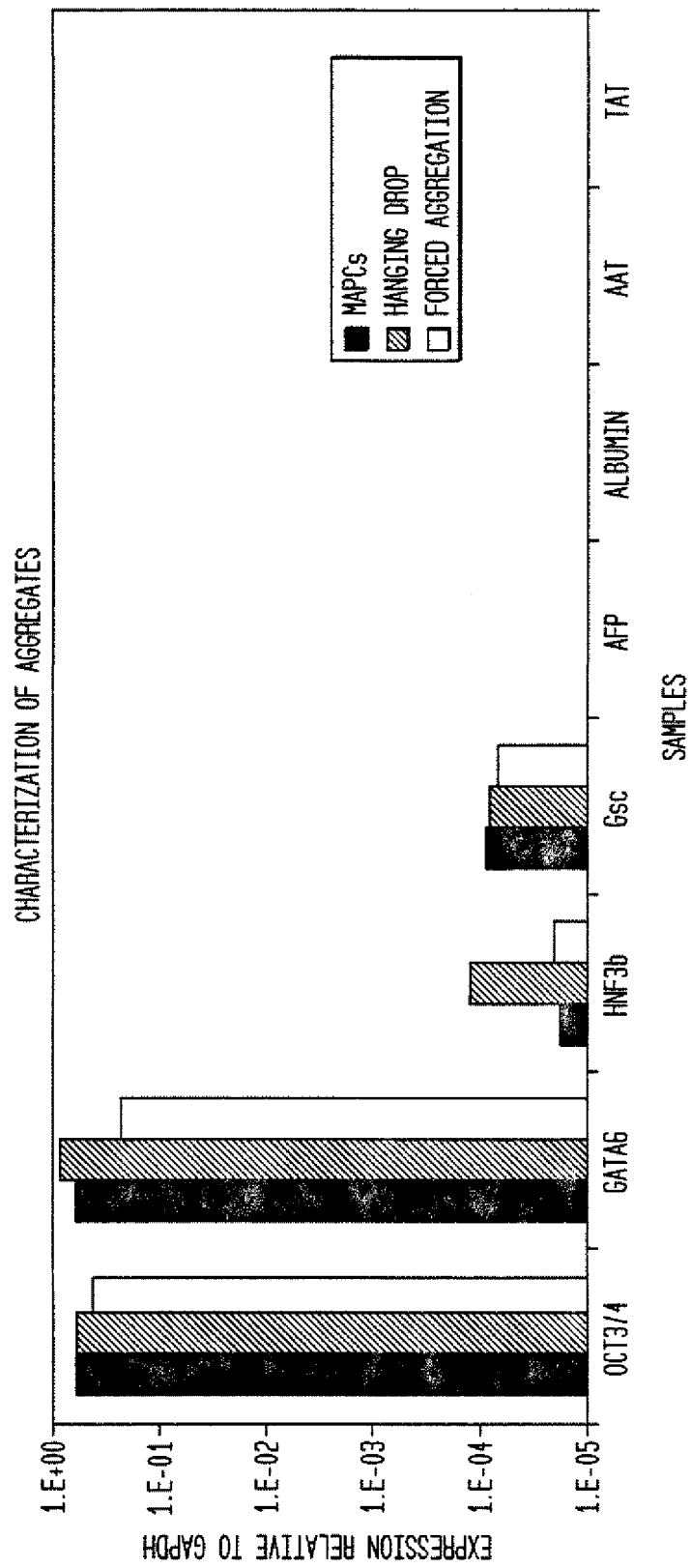
FIG. 8 shows characterization of MAPC aggregates using QRT-PCR.
Figure 9:
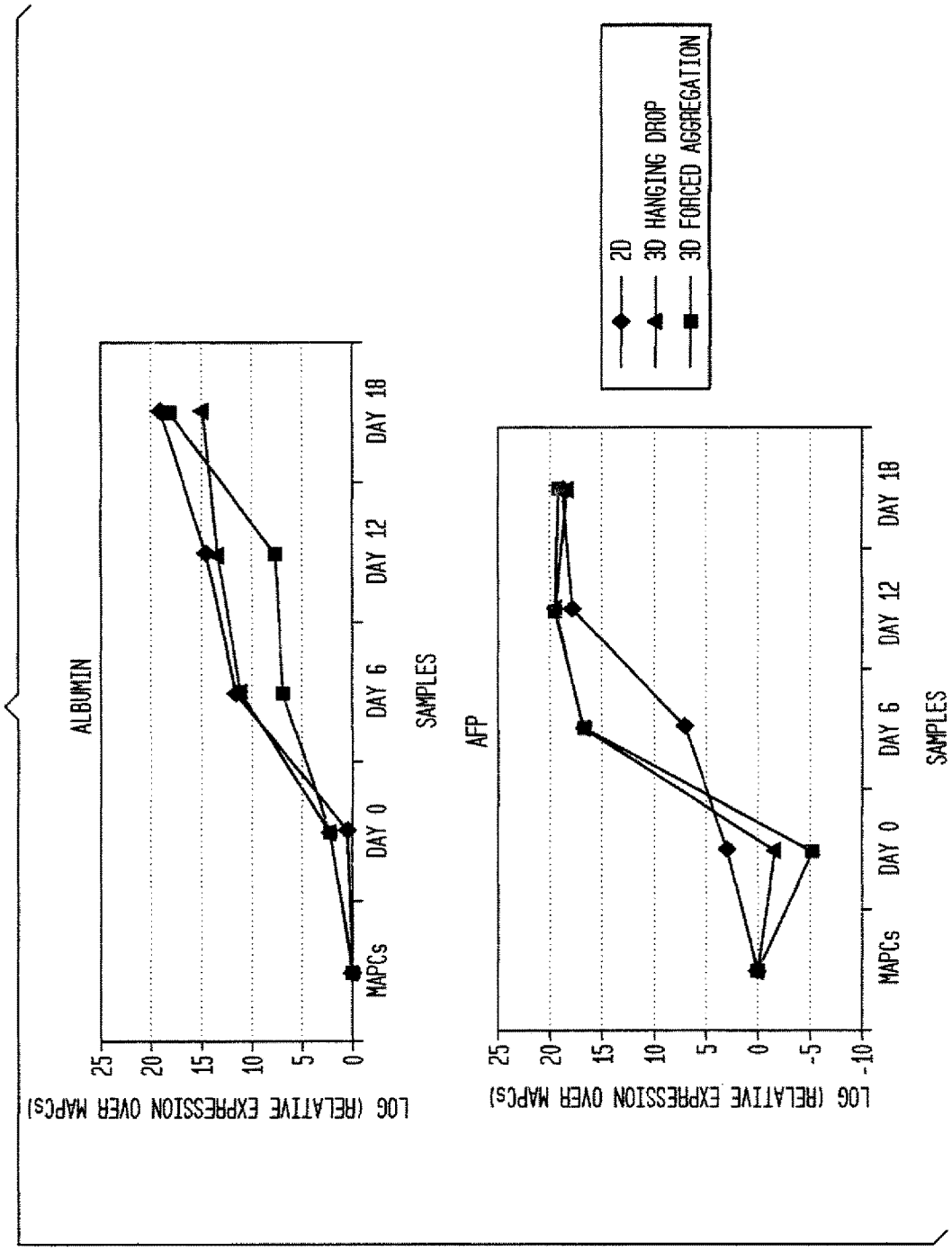
FIG. 9 shows results of differentiation using a multi-step protocol.
Figure 10:
FIG. 10 shows morphology of aggregates after 21 days of differentiation (10×).

As used herein, the terms below are defined by the following meanings.

"2D" refers to cell culture where cells grow by attaching (adhering) to a substrate. Such cells form monolayers or colonies where the cells are each attached to a substrate (where the substrate is other than the cells themselves).

"3D" refers to cell culture where cells grow as an aggregate through association of the cells with each other and not through association with a substrate other than the cells themselves. In the art, "3D" may refer to growth of cells on a scaffold or matrix. But, as used herein, 3D is used as above.

In one embodiment, cells can be initially grown on a substrate where some cells associate with (adhere to) the substrate but further growth forms cell-cell associations (aggregation) that do not depend on association (adherence) of the further-grown cells with the substrate. A cellular feeder layer is also considered a substrate. So attachment of cells to a feeder layer is also a form of adherent culture (not an aggregate) since attachment of the cells is not to each other but to the cells in the feeder layer.

"A" or "an" means one or more than one.

"Aggregate" refers to an association of cells in which the association is caused by cell-cell interaction rather than adherence to a substrate. In 2D monolayer culture, cells are "associated" with each other but by means of attachment to a substrate material, such as plastic or surface coating. In an aggregate, two or more cells associate with each other by biologic attachments to one another. This can be through surface proteins, such as extracellular matrix proteins.

"Co-administer" can include simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Cytokines" refer to cellular factors that induce or enhance cellular movement, such as homing of stem cells, progenitor cells or differentiated cells such as skeletal myoblasts, cardiac myoblasts, myocytes, and the like. Cytokines may also stimulate such cells to divide.

"Definitive endodermal phenotype" is a particular phenotype of cells that no longer express oct3/4, do not express the primitive endoderm gene Sox7, do not express the mesodermal gene Flk1, but do express Sox17, Foxa2, E-cadherin, CXCR4, and PDGF-Ra.

"Differentiation factor" refers to a cellular or chemical factor, preferably growth factor or angiogenic factor, that acts on stem or progenitor cells to form more highly differentiated progeny.

"Dispersion" refers to cells derived from the aggregates and which retain the function of the cells in aggregate form in that they can still differentiate into cell types of more than one embryonic germ layer.

An "effective amount" generally means an amount which provides the desired local or systemic effect, such as enhanced performance. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, injury and/or disease or injury being treated and amount of time since the injury occurred or the disease began. One skilled in the art, specifically a physician, would be able to determine the number of cells that would constitute an effective dose.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"EC cells" were discovered from analysis of a type of cancer called a teratocarcinoma. In 1964, researchers noted that a single cell in teratocarcinomas could be isolated and remain undifferentiated in culture. This type of stem cell became known as an embryonic carcinoma cell (EC cell).

"Embryonic stem cells" are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta.

"Expansion" refers to the propagation of a cell without differentiation.

"Hepatic differentiation factors" are chemical or biological factors that induce differentiation of stem and progenitor cells into more differentiated cells of the hepatic lineage. Hepatic differentiation factors include, but are not limited to, Wnt3a, ActivinA, bFGF, BMP4, aFGF, FGF4, FGF8b, HGF and Follistatin. The initial cell may express oct3/4.

"Hepatoblast phenotype" is a particular phenotype of cells that co-express albumin, alpha fetoprotein and keratin 19, and express, on the cell membrane, c-Met, EPCAM, and Dlk1 (Tanimizu et al., *J Cell Sci* 116:1775-1786 (2003)).

"Hepatocyte phenotype" is a particular phenotype of cells that express albumin and keratin 18 but not alpha fetoprotein and keratin 19; in addition, hepatocytes may express one or more of TAT, MRP2, G6P, GLYS2, PEPCK, A1AT, BSEP, CX-32, NTCP, CYP7A1 (rat) and CYP3A4 (human).

Use of the term "includes" is not intended to be limiting. For example, stating that stem cells "include" IPS cells does not mean that other stem cells are excluded.

"Induced pluripotent stem cells (IPSC or IPS cells)" are somatic cells that have been reprogrammed. for example, by introducing exogenous genes that confer on the somatic cell a less differentiated phenotype. These cells can then be induced to differentiate into more differentiated progeny. IPS cells have been derived using modifications of an approach originally discovered in 2006 (Yamanaka et al., *Cell Stem Cell* 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861 (2008); Jaenisch et al., *Cell* 132:567-582 (2008); Hanna et al., *Cell* 133:250-264 (2008); and Brambrink et al., *Cell Stem Cell* 2:151-159 (2008). These references are incorporated by reference for teaching IPSCs and methods for producing them. It is also possible that such cells can be created by specific culture conditions (exposure to specific agents).

The term "isolated" refers to a cell that is not associated with one or more cells or one or more cellular components that are associated with the cell in vivo. An "enriched population" means a relative increase in numbers of a desired cell relative to one or more other cell types in vivo or in primary culture.

However, as used herein, the term "isolated" does not indicate the presence of only a specific desired cell, such as a stem or progenitor cell. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings. For example, a cell may undergo 10, 20, 30, 40 or more doublings in vitro or ex vivo so that it is enriched compared to its original numbers in vivo or in its original tissue environment (e.g., bone marrow, peripheral blood, umbilical cord blood, adipose tissue, etc.)

"Liver-committed endodermal phenotype" is a particular phenotype of cells that are EPCAM positive and Dlk1 Negative (Tanimizu et al., *J Cell Sci* 116:1775-1786 (2003)).

"MAPC" is an acronym for "multipotent adult progenitor cell". It refers to a non-embryonic stem cell that can give rise to cell types of all three germ layers (i.e., endoderm, mesoderm and ectoderm) upon differentiation. Like embryonic stem cells, human MAPCs can express one or more of telomerase, oct3/4 (i.e., oct3A), rex-1, rax-1, sox-2, SSEA-4, and may express nanog. The term "adult" in. MAPC is non-restrictive. It refers to a non-embryonic somatic cell. MAPCs are reported to express high levels of telomerase (Jiang et al., *Nature* 418:41 (2002); *Exp Hematol* 30:896 (2002)) (incorporated by reference for teaching telomerase expression). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs. MAPCs are karyotypically normal.

"Multipotent," with respect to the term in "MAPC," refers to the ability to give rise to cell lineages of more than one primitive germ layer (i.e., endoderm, mesoderm and ectoderm) upon differentiation, such as all three. This term is not used consistently in the literature.

"Primitive endodermal phenotype" is a particular phenotype of cells that may express sox7, sox17, gata4, gata6, Cited1, Tcf2, Lamb1, Dab2, LamA1, LamA4, Lamc1, Co14a1, and Nidogen2 (this is a phenotype of mouse and rat MAPC, XEN cells from J. Rossant and Sox7 expressing ESC from J. Rossant. See also Ulloa-Montoya et al., *Genome Biol* 8:R163 (2007); Se'guin et al., *Cell Stem Cell* 3:182-195 (2008); and Kunath et al., *Development* 132:1649-1661 (2005)).

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage.

"Self-renewal" refers to the ability to produce replicate daughter stem cells having the same differentiation potential as the parental cells. A similar term used in this context is "proliferation."

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., *Nature* 385:810-813 (1997); Ying et al., *Nature* 416:545-548 (2002); Guan et al., *Nature* 440:1199-1203 (2006); Takahashi et al., *Cell* 126:663-676 (2006); Okita et al., *Nature* 448:313-317 (2007); and Takahashi et al., *Cell* 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources, such as embryoid bodies (although these can be considered embryonic stem cells in that they are derived from embryonic tissue, although not directly from the inner cell mass).

A "subject" is a vertebrate, preferably a mammal, more preferably a human. Mammals include, but are not limited to, humans, farm animals, sport animals, and pets. Subjects in need of treatment by methods of the present invention include those suffering from a loss of function as a result of physical or disease-related damage.

The term "therapeutically effective amount" refers to the amount determined to produce any therapeutic response in a mammal. For example, effective amounts of the therapeutic cells or cell-associated agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

The inventors have discovered that non-embryonic stem cells can be grown as aggregates and the aggregates comprise cells that retain the undifferentiated phenotype of the non-embryonic stem cells. Therefore, the aggregates are capable of producing progeny with a more differentiated phenotype. The ability to form aggregates can be useful for large scale cell production.

Stem cells that are useful for the invention may include cells that are not transformed or tumorigenic. They may have a normal karyotype. For example, some, such as MAPC, are known not to form teratomas in vivo and to have a normal karyotype in culture.

The aggregate can be formed by using any method for non-adherent growth, such as, any of the known methods in the art. These include, but are not limited to, the hanging drop method (Kurosawa and Hopfl, cited below), the forced aggregation method (centrifugation) (Ng, cited below), methods wherein the cells are cultured on non-adherent plastic, suspension culture (static or stirred), bioreactor expansion platforms, and non-attachment or special coating e.g., temperature-sensitive polymer-based plates, microcontact printing of wells to control size of colonies, and microfluidic devices.

Many different basal media are known in the art. Such media may be used with or without serum (or at varying serum concentrations, e.g., 0.5%-20% or more). When serum is absent or reduced, the person of ordinary skill would know to use growth factors to complement the basal medium, including, but not limited to, EGF and/or PDGF. Oxygen concentrations may be reduced from atmospheric to ranges of 1-5, 5-10, 10-15, 15-20% and numbers between.

The stem cells that form the aggregates can be derived from various tissues, such as bone marrow, placenta, peripheral blood, umbilical cord blood and tissue, skin, and fat. Cells designated "MAPC" in the literature are exemplified in this application. But the invention further contemplates any non-embryonic stem cell that forms cell types of more than one embryonic germ layer. See, for example, U.S. Pat. No. 7,311,905; 2003/0059414; 2002/0164794, all incorporated by reference for teaching these cells and methods for making them.

In addition, less differentiated stem cells may be derived by various manipulations, such as, by transfecting and expressing certain genes in differentiated cells to genetically reprogram the undifferentiated state, nuclear transfer of somatic cells into an environment that creates gene expression corresponding to a less differentiated phenotype than was present in the somatic cell, growth in media and culture conditions sufficient to maintain pluripotency (for example, "MAPC media" and expansion protocols), nuclear reprogramming by fusion of somatic cells with embryonic stem cells, culture-induced reprogramming-cell explantation, and treatment of somatic nuclei with cell extract from oocytes or pluripotent cells (Hochedlinger and Jaenisch, *Nature* 441: 1061-1067 (2006)).

The invention pertains to stem cells from any species and, particularly, mammalian species and, more particularly, to humans. Within a species, uses (e.g., administration of cells to a subject) can be of allogeneic cells. Across species, uses can be of xenogeneic cells. In a subject, cells can be autologous.

An aggregate, with respect to the invention, is defined as at least ten cells. But ranges include aggregates that are not so large that the inner cells become necrotic. This can include aggregates of 100-300μ and numbers in between, such as 150-250μ. The skilled person would recognize any useful number in that range. A useful number of aggregates would be greater than 50 for clinical applications. Cell numbers are variable and range from hundreds to ten of thousands or greater, e.g., 100-1000 (about 200, 300, 400, 500, 600, 700, 800, 900 cells), 1000-10,000, (about 2000, 3000, 4000, 5000, 6000, 7000, 8000, 9000 cells), 10,000-50,000 (about 20,000; 30,000; 40,000 cells) or more, etc.

The examples provided in this application utilize a cell that has been designated multipotent adult progenitor cell ("MAPC"). But the invention pertains to any and all stem cells that are not embryonic cells but can differentiate into all types of more than one germ layer (e.g., two or three).

Another parameter in forming aggregates is the purity of the isolated stem cell population used to form aggregates. Accordingly, in the present invention, aggregates may be formed of a desired stem cell that is present in a population containing other cells as well. Bone marrow cells, for example, comprise mixed populations of cells, which can be purified to a degree sufficient to produce a desired effect. Those skilled in the art can readily determine the percentage of a desired stem cell in a population using various well-known methods, such as fluorescence activated cell sorting (FACS). Purity of a given stem cell can also be determined according to the gene expression profile within a population.

Ranges of purity in populations comprising a given stem cell are about 50-55%, 55-60%, and 65-70%. Other ranges include purity of about 70-75%, 75-80%, 80-85%. Still other ranges include purity of about 85-90%, 90-95%, and 95-100%. However, populations with lower purity can also be useful, such as about 25-30%, 30-35%, 35-40%, 40-45% and 45-50%.

In the aggregates, the non-embryonic cells, such as MAPC, may be substantially homogeneous or be found in less than substantially homogeneous form. Purity, therefore, in the aggregate can vary as above. Furthermore, other cell types can be mixed in when forming the aggregates.

In methods in which the aggregate is subjected to differentiation conditions to produce some of the differentiated cell types discussed in this application, many, if not most of those conditions are available to those of ordinary skill in the art. See for example, Mays et al., *Expert Opinion Biol Ther* 2:173-184 (2007) and links therein to differentiation protocols; hepatocytes (*J Clin Invest* 109:1291-302; hematopoietic (*J Exp Med* 204:129-39), smooth muscle (*J Clin Invest* 116:3139-3149 (2006)). These differentiation conditions are incorporated herein by reference. Many differentiation conditions are in U.S. Pat. No. 7,015,037 and Mays et al. (above), incorporated by reference for these protocols.

One protocol for forming the aggregates is using DMEM-low glucose, MCDB, 2% Fetal Calf Serum, PDGF-BB, EGF, LIF, BSA, insulin-selenium-transferrin (ITS), linoleic acid and lipid mixture and 5% Oxygen. It may be preferable to use conditions that enhance expression of oct3/4 transcription factor, for example, at the levels expressed in MAPCs in 2D (adherent) cultures.

Aggregation Methods

There are at least two methods to form the aggregates: (a) hanging drop (surface tension based method); and (b) forced aggregation (physically centrifuging cells at 1500 rpm, 4 minutes onto the bottom of 96 well Ultra-low attachment U bottom plate (Corning). Although both methods are usable to form aggregates, the hanging drop method is more cost-effective to produce large number of aggregates. Other ways include stirred suspension or growth in a non-attachment plate/flask. Other potential methods of forming controlled-size aggregates would be methods such as microcontact printing.

These methods are illustrated below in the following citations, which are hereby incorporated by reference for teaching various non-adherent cell culture methods.

Dang et al., "Efficiency of embryoid body formation and hematopoietic development from embryonic stem cells in different culture systems" *Biotechnology and Bioengineering* 78: 442-453 (2002).

Konno et al., "Formation of embryoid bodies by mouse embryonic stem cells on plastic surfaces" *Journal of Bioscience and Bioengineering* 100:88-93 (2005).

Ng et al., Forced aggregation of defined numbers of human embryonic stem cells into embryoid bodies fosters robust, reproducible hematopoietic differentiation. Commentary" *Blood* 106:1601-1603 (2005) [Forced aggregation method].

Kurosawa et al., "A simple method for forming embryoid body from mouse embryonic stem cells" *Journal of Bioscience and Bioengineering* 96: 409-411 (2003).

Magyar et al., "Mass production of embryoid bodies in microbeads" *Annals of the New York Academy of Sciences* 944: 135-143 (2001). [Scalable production of cell aggregates as microbeads].

Hopfl et al., "Differentiating embryonic stem cells into embryoid bodies" *Methods Mol Biol* 254:79-98 (2004) [Hanging drop method].

Cameron et al., "Improved development of human embryonic stem cell-derived embryoid bodies by stirred vessel cultivation" *Biotechnol Bioeng* 94:938-948 (2006) [Stirred-suspension culture system].

Wang et al., "Scalable producing embryoid bodies by rotary cell culture system and constructing engineered cardiac tissue with ES-derived cardiomyocytes in vitro" *Biotechnol Prog* 22:811-818 (2006) [Rotary suspension systems].

Yang et al., *Biomacromolecules* 8, 9, 2746-2752 (2007) [Use of temperature sensitive hydrogel].

Torisawa et al., "Lab on a Chip" 7:770-776 (2007) [Use of microfluidics for efficient EB size formation].

The aggregates can be formed with a starting cell number greater than 100. A maximum of 4000 cells have been used to form a single aggregate over 4 days of Hanging drop/Forced aggregation method. Starting from 1000 cells, the aggregates had an approximate number of 6600 cells/aggregate (counted by trypan blue exclusion method) after 4 days of hanging drop culture. Therefore, a useful starting range could be 100-4000 for each aggregate with the most optimum being between 400-2000.

Stem Cells

The present invention can be practiced, preferably, using stem cells of vertebrate species, such as humans, non-human primates, domestic animals, livestock, and other non-human mammals.

Non-Embryonic

Non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269; umbilical cord matrix (Mitchell et al., *Stem Cells*, 21:50-60, 2003), small embryonic-like stem cells (Kucia et al., *J Physiol Pharmaco*, 57 Suppl 5:5-18, 2006), amniotic fluid stem cells (Atala, A., *J Tissue Regen Med* 1:83-96, 2007), skin-derived precursors (Toma et al., *Nat Cell Biol* 3:778-784, 2001), adipose tissue (U.S. 2005/0153442), gastrointestinal stem cells, epidermal stem cells, and hepatic stem cells, which also have been termed "oval cells" (Potten et al., *Trans R Soc Lond B Biol Sci* 353:821-830 (1998); Watt, F., *Trans R Soc Lond B Biol Sci* 353:831 (1997); Alison et al., *Hepatology* 29:678-683 (1998), and bone marrow (see U.S. Publication Nos. 2003/0059414 and 2006/0147246), each of which is incorporated by reference herein for teaching these cells.

Strategies of Reprogramming Somatic Cells

Several different strategies, such as nuclear transplantation, cellular fusion, and culture induced reprogramming, have been employed to induce the conversion of differentiated cells into an embryonic state. The references cited below are incorporated by reference for teaching how to make these cells and describing them.

Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature* 441:1061-1067 (2006) and Yamanaka, S., *Cell Stem Cell* 1:39-49 (2007)).

Nuclear Transfer

Nuclear transplantation (NT), also referred to as somatic cell nuclear transfer (SCNT), denotes the introduction of a nucleus from a donor somatic cell into an enucleated oocyte to generate a cloned animal (Wilmut et al., *Nature* 385:810-813 (1997). The generation of live animals by NT demonstrated that the epigenetic state of somatic cells, including that of terminally differentiated cells, can be reprogrammed to an embryonic state.

Fusion of Somatic Cells and Embryonic Stem Cells

Epigenetic reprogramming of somatic nuclei to an undifferentiated state has been demonstrated by fusion of embryonic cells with somatic cells. Hybrids between various somatic cells and embryonic carcinoma cells (Softer, D., *Nat*

Rev Genet 7:319-327 (2006), embryonic germ (EG), or ES cells (Zwaka and Thomson, *Development* 132:227-233 (2005)) share many features with the parental embryonic cells, indicating that the pluripotent phenotype is dominant in such fusion products. As with mouse (Tada et al., *Curr Biol* 11:1553-1558 (2001)), human. ES cells have the potential to reprogram somatic nuclei after fusion (Cowan et al., *Science* 309:1369-1373 (2005)); Yu et al., *Science* 318: 1917-1920 (2006)). Activation of silent pluripotency markers, such as oct4, may occur (Do and Scholer, *Stem Cells* 22:941-949 (2004)). Forced overexpression of Nanog in ES cells promotes pluripotency when fused with neural stem cells (Silva et al., *Nature* 441:997-1001 (2006)).

Culture-Induced Reprogramming

Pluripotent cells have been derived from embryonic sources, such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol* 7:881-884 (1997)); embryonic stem cells have been derived from blastomeres (Wakayama et al., *Stem Cells* 25:986-993 (2007)); inner cell mass cells (source not applicable) (Eggan et al., *Nature* 428:44-49 (2004)); embryonic germ and embryonal carcinoma cells have been derived from primordial germ cells (Matsui et al., *Cell,* 70:841-847 (1992)); GMCS, maSSC, and MASC have been derived from spermatogonial stem cells (Guan et al., *Nature,* 440:1199-1203 (2006); Kanatsu-Shinohara et al., *Cell* 119:1001-1012 (2004); and Seandel et al., *Nature* 449:346-350 (2007)); EpiSC cells are derived from epiblasts (Brons et al., *Nature* 448:191-195 (2007); Tesar et al., *Nature,* 448:196-199 (2007)); parthogenetic ES cells have been derived from human oocytes (Cibelli et al., *Science* 295L819 (2002); Revazova et al., *Cloning Stem Cells* 9:432-449 (2007)); human ES cells have been derived from human blastocysts (Thomson et al., *Science* 282:1145-1147 (1998)); MAPC have been derived from bone marrow (Jiang et al., *Nature,* 418:41-49 (2002); Phinney and Prockop, *Stem Cells* 25:2896-2902 (2007)); cord blood cells (derived from cord blood) (van de Ven et al., *Exp Hematol* 35:1753-1765 (2007)); neurosphere derived cells derived from neural cell (Clarke et al., *Science,* 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell,* 119:1001-1012 (2004) or maGSCs (Guan et al., *Nature* 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline. Recently, multipotent adult spermatogonial stem cells (MASCs) were derived from testicular spermatogonial stem cells of adult mice, and these cells had an expression profile different from that of ES cells (Seandel et al., *Nature* 449:346-350 (2007)) but similar to EpiSC cells, which were derived from the epiblast of postimplantation mouse embryos (Brons et al., *Nature* 448:191-195 (2007); Tesar et al., *Nature* 448:196-199 (2007)).

Reprogramming by Defined Transcription Factors

Somatic cells can be reprogrammed to an ES-like state (Takahashi and Yamanaka, *Cell* 126:663-676 (2006)). Mouse embryonic fibroblasts (MEFs) and adult fibroblasts were programmed to pluripotent ES-like cells by transduction of oct4, sox2, c-myc, and Klf4. Cells were called iPS (induced pluripotent stem) cells. While genetic experiments had established that Oct4 and Sox2 are essential for pluripotency (Chambers and Smith, *Oncogene* 23:7150-7160 (2004); Ivanona et al., *Nature* 442:5330538 (2006); Masui et al., *Nat Cell Biol* 9:625-635 (2007)), c-myc and Klf4 may be dispensable (Nakagawa et al., *Nat Biotechnol* 26:191-106 (2008); Werning et al., *Nature* 448:318-324 (2008); Yu et al., *Science* 318: 1917-1920 (2007)).

MAPC

An exemplary cell of the present invention has been designated "MAPC." MAPC is an acronym for "multipotent adult progenitor cell" (non-ES, non-EG, non-germ) that has the capacity to differentiate into cell types of all three primitive germ layers (ectoderm, mesoderm, and endoderm). Genes found in ES cells also have been found in MAPCs (e.g., telomerase, Oct 3/4, rex-1, rox-1, sox-2). Oct 3/4 (Oct 3A in humans) appears to be specific for ES and germ cells. MAPC represents a more primitive progenitor cell population than MSC and demonstrates differentiation capability encompassing the epithelial, endothelial, neural, myogenic, hematopoietic, osteogenic, hepatogenic, chondrogenic and adipogenic lineages (Verfaillie, C. M., *Trends Cell Biol* 12:502-8, 2002, Jahagirdar et al., *Exp Hematol* 29:543-56, 2001; Reyes and Verfaillie, *Ann N Y Acad Sci* 938:231-233, 2001; Jiang et al., *Exp Hematol* 30896-904, 2002; and Jiang et al., *Nature* 418:41-9, 2002). MAPCs thus emulate the broad biological plasticity characteristic of ES cells, while maintaining the other characteristics that make non-embryonic stem cells appealing (e.g., normal karyotype and does not form teratomas).

Human MAPCs are described in U.S. Pat. No. 7,015,037 and application Ser. No. 10/467,963, the contents of which are incorporated herein by reference for their description of MAPCs. MAPCs have been identified in other mammals. MAPCs can be isolated from multiple sources, including, but not limited to, bone marrow, placenta, umbilical cord and cord blood, muscle, brain, liver, spinal cord, blood and skin.

Isolation and Growth of MAPCs

Prior to forming aggregates, MAPCs can be isolated and cultured using methods disclosed herein and in U.S. Pat. No. 7,015,037, which is incorporated by reference herein for these methods.

In addition, the density at which MAPCs are cultured can vary from about 100 cells/cm$^2$ to about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3-5%, can be used at any time during the isolation, growth and differentiation.

In an embodiment specific for MAPCs, supplements are cellular factors or components that allow MAPCs to retain the ability to differentiate into all three lineages. This may be indicated by the expression of specific markers of the undifferentiated state. MAPCs, for example, constitutively express Oct 3/4 (Oct 3A) and maintain high levels of telomerase. Assays for monitoring gene expression are well known in the art (e.g., RT-PCR) and can be conducted using standard methodology.

Cell Culture

Cells may be cultured in low-serum or serum-free culture medium. Serum-free medium used to culture MAPCs is described in U.S. Pat. No. 7,015,037. Many cells have been grown in serum-free or low-serum medium. In this case, the medium is supplemented with one or more growth factors. Commonly used growth factors include, but are not limited to, bone morphogenic protein, basic fibroblast growth factor, platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference herein for teaching growing cells in serum-free medium.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads and combinations thereof. One embodiment of the present invention contemplates the use of FACS to identify and separate cells based on cell-surface antigen expression.

Pharmaceutical Formulations

Any of the cells produced by the methods described herein can be used in the clinic to treat a subject. They can, therefore, be formulated into a pharmaceutical composition. Therefore, in certain embodiments, the cells are present within a composition adapted for and suitable for delivery, i.e., physiologically compatible. Accordingly, compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

In other embodiments, cells are present within a composition adapted for or suitable for freezing or storage.

In many embodiments the purity of the cells for administration to a subject is about 100%. In other embodiments it is 95% to 100%. In some embodiments it is 85% to 95%. Particularly in the case of admixtures with other cells, the percentage can be about 10%-45%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The numbers of cells in a given volume can be determined by well known and routine procedures and instrumentation. The percentage of the cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering the cells for a given application will depend on a variety of factors. Prominent among these will be the species of subject, the nature of the disorder, dysfunction, or disease being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of administration and the nature of the particular dosage form.

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic cells. Various embodiments of the invention comprise measures to increase cell survival and/or to overcome problems posed by barriers to seeding and/or growth.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. This final formulation is by definition the cells in a pharmaceutically-acceptable carrier.

The cells are subsequently placed in a syringe or other injection apparatus for precise placement at the site of the tissue defect. The term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200µ I.D.) or even 30 gauge (150µ I.D.) are desirable. The maximum particle size that can be extruded through such needles will be a complex function of at least the following: particle maximum dimension, particle aspect ratio (length:

width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The desired isotonicity of the compositions of this invention may be accomplished using sodium chloride, or other pharmaceutically-acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically-acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically-acceptable preservative or stabilizer can be employed to increase the life of cell/medium compositions. If such preservatives are included, it is well within the purview of the skilled artisan to select compositions that will not affect the viability or efficacy of the cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

In some embodiments, cells are formulated in a unit dosage injectable form, such as a solution, suspension, or emulsion. Pharmaceutical formulations suitable for injection of cells typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

In some embodiments cells are encapsulated for administration, particularly where encapsulation enhances the effectiveness of the therapy, or provides advantages in handling and/or shelf life. Encapsulation in some embodiments where it increases the efficacy of cell mediated immunosuppression may, as a result, also reduce the need for immunosuppressive drug therapy.

Also, encapsulation in some embodiments provides a barrier to a subject's immune system that may further reduce a subject's immune response to the cells (which generally are not immunogenic or are only weakly immunogenic in allogeneic transplants), thereby reducing any graft rejection or inflammation that might occur upon administration of the cells.

Cells may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of cells are known to those of skill in the art and are described, for example, in Chang et al., 1999; Matthew et al., 1991; Yanagi et al., 1989; Cai et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of cells.

Certain embodiments incorporate cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

In the case of treating liver deficiency, in particular, the cells may be enclosed in a device that can be implanted in a subject. Cells can be implanted in or near the liver or elsewhere to replace or supplement liver function. Cells can also be implanted without being in a device, e.g., in existing liver tissue.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells appropriate to be used in accordance with various embodiments of the invention will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells to be effective; and such characteristics of the site such as accessibility to cells and/or engraftment of cells. Additional parameters include co-administration with other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

The optimal dose of cells for some embodiments will be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5 \times 10^5$ to $5 \times 10^6$ cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells may be administered in an initial dose, and thereafter maintained by further administration. Cells may be administered by one method initially, and thereafter administered by the same method or one or more different methods. The levels can be maintained by the ongoing administration of the cells. Various embodiments administer the cells either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments cells are administered to a subject in one dose. In others cells are administered to a subject in a series of two or more doses in succession. In some other embodiments wherein cells are administered in a single dose, in two doses, and/or more than two doses, the doses may be the same or different, and they are administered with equal or with unequal intervals between them.

Cells may be administered in many frequencies over a wide range of times. In some embodiments, they are administered over a period of less than one day. In other embodiment they are administered over two, three, four, five, or six days. In some embodiments they are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Uses

Useful cells are in aggregate form or in cells derived from the aggregate. Large numbers of cells can be produced by aggregation methods but the cells that are further used can be removed, e.g., dis-aggregated or dispersed from the aggregate. So, for example, pharmaceutical compositions can comprise the cells in aggregate form or derived from the aggregate (e.g., by dispersion). Likewise, differentiation factors can be applied to the cells in aggregate form or to cells derived from the aggregate. Pharmaceutical compositions can, therefore, be made with differentiated cells formed by applying differentiation conditions to the aggregate or to cells derived from the aggregate. Further, clinical uses described below pertain to the in vivo use of the undifferentiated aggregates and undifferentiated cells derived from the aggregates as well as differentiated progeny of the aggregates and differentiated progeny of cells derived from the aggregates. Undifferentiated cells are useful, like their differentiated progeny, because they may give rise to those progeny in vivo. (Undifferentiated cells may be useful even when they do not differentiate, for other beneficial purposes, such as angiogenic, immunomodulatory, cytogenic, trophic, etc.).

The aggregated cells or cells derived from the aggregates may have the capacity to be induced to differentiate to form at least one differentiated cell type of mesodermal, neurectodermal and endodermal origin. For example, the cells may have the capacity to be induced to differentiate to form cells of at least osteoblast, chondrocyte, adipocyte, fibroblast, marrow stroma, skeletal muscle, smooth muscle, cardiac muscle, endothelial, epithelial, hematopoietic, glial, neuronal or oligodendrocyte cell type.

The invention further provides differentiated cells obtained from the cells described above, wherein the progeny cell may be a bone, cartilage, adipocyte, fibroblast, marrow stroma, skeletal muscle, smooth muscle, cardiac muscle, endothelial, epithelial, endocrine, exocrine, hematopoietic, glial, neuronal or oligodendrocyte cell. The differentiated progeny cell may be a skin epithelial cell, liver epithelial cell, pancreas epithelial cell, pancreas endocrine cell or islet cell, pancreas exocrine cell, gut epithelium cell, kidney epithelium cell, or an epidermal associated structure.

The cells or their differentiated progeny can be used to correct a genetic disease, degenerative disease, cardiovascular disease, metabolic storage disease, neural, or cancer disease process. They can be used to produce gingiva-like material for treatment of periodontal disease. They can be used to develop skin epithelial tissue derived from the cells that can be utilized for skin grafting and plastic surgery. They can be used to enhance muscle, such as in the penis or heart. They can be used to produce blood ex vivo for therapeutic use, or to produce human hematopoietic cells and/or blood in prenatal or post natal animals for human use. They can be used as a therapeutic to aid for example in the recovery of a patient from chemotherapy or radiation therapy in treatment of cancer, in the treatment of autoimmune disease, to induce tolerance in the recipient. They can be used to treat AIDS or other infectious diseases.

Neuroretinal cells can be used to treat blindness caused by among other things but not limited to neuroretinal disease caused by among other things macular degeneration, diabetic retinopathy, glaucoma, retinitis pigmentosa.

The cells or cardiomyocytes derived from the cells can be used to treat cardiac diseases including, but not limited to, myocarditis, cardiomyopathy, heart failure, damage caused by heart attacks, hypertension, atherosclerosis, and heart valve dysfunction. They also can be used to treat a disease involving CNS deficits or damage. Further the stem cell, or its neuronally differentiated progeny cell, can be used to treat a disease involving neural deficits or degeneration including, but not limited to, stroke, Alzheimer's disease, Parkinson's disease, Huntington's disease, AIDS-associated dementia, spinal cord injury, and metabolic diseases affecting the brain or other nervous tissue.

Cells or their differentiated progeny, such as stromal cells, can be used to support the growth and differentiation of other cell types in vivo or in vitro, including, but not limited to, hematopoietic cells, pancreatic islet or beta cells, hepatocytes, and the like. The cells or differentiated cartilage progeny, can be used to treat a disease of the joints or cartilage, including, but not limited to, cartilage tears, cartilage thinning, and osteoarthritis. Moreover, the cells or their differentiated osteoblast progeny can be used to ameliorate a process having deleterious effects on bone including, but not limited to, bone fractures, non-healing fractures, osteoarthritis, "holes" in bones cause by tumors spreading to bone such as prostate, breast, multiple myeloma, and the like.

Using appropriate growth factors, chemokines, and cytokines, cells can be induced to differentiate to form a number of lineages, including, for example, a variety of cells of mesodermal phenotype, cells of neuroectodermal phenotype (glial cells, oligodendrocytes, and neurons), and cells of endodermal phenotype. These include osteoblasts, chondroblasts, adipocyte, cartilage and bone, skeletal muscle, smooth muscle, cardiac muscle, endothelial cells, hematopoietic cells, stromal cells, neuronal cells, and epithelial cells.

Osteoblasts:
Cells that have been induced to differentiate to form bone cells can be used as cell therapy or for tissue regeneration in osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.

Chondrocytes:
Cells that have been induced to differentiate to form cartilage cells can be used for cell therapy or tissue regeneration in age-related diseases or injuries, in sports-related injuries, or in specific diseases, such as rheumatoid arthritis, psoriasis arthritis, Reiter's arthritis, ulcerative colitis, Crohn's disease, ankylosing spondylitis, osteoarthritis, reconstructive surgery of the outer ear, reconstructive surgery of the nose, and reconstructive surgery of the cricoid cartilage.

Adipocytes:
Cells that have been induced to differentiate to form adipocytes can be used in resculpting for reconstructive or cosmetic surgery, including but not limited to, breast reconstruction after mastectomy, reshaping tissue lost as a result of other surgery, such as tumor removal from the face or hand, breast augmentation, and reduction of wrinkles. Treatment of Type II diabetes is also applicable. Adipocytes thus derived can also provide an effective in vitro model system for the study of fat regulation.

Fibroblasts:
Fibroblasts derived from the cells can be used for cell therapy or tissue repair to promote wound healing or to provide connective tissue support, such as scaffolding for cosmetic surgery.

Skeletal Muscle:
Cells that have been be induced to differentiate to form skeletal muscle cells can be used for cell therapy or tissue repair in the treatment of Duchenne muscular dystrophy, Becker muscular dystrophy, myotonic dystrophy, skeletal myopathy, and reconstructive surgery to repair skeletal muscle damage.

Smooth Muscle:
Cells that have been induced to differentiate to form smooth muscle cells can be used for cell therapy or tissue repair in the treatment of developmental abnormalities of the gastrointestinal system, such as oesophageal atresia, intestinal atresia, and intussusception, and replacement of tissues after surgery for bowel infarction or colostomy. Smooth muscle cells can also be used for bladder or uterine reconstruction, neovascularization, repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues.

Cardiomyocytes:
Cardiomyocytes can be used for cell therapy or tissue repair for treating heart tissue damaged following myocardial infarction, in conjunction with congestive heart failure, during valve replacement, by congenital heart anomalies, or resulting from cardiomyopathies or endocarditis.

Microglial Cells:
Microglial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, and for regeneration after spinal cord injury.

Stromal Cells:

Stromal cells can be used as transplant cells for post-chemotherapy bone marrow replacement and bone marrow transplantation.

Endothelial Cells:

Endothelial cells can be used in the treatment of Factor VIII deficiency and to produce angiogenesis for neovascularization. Endothelial cells can also provide an in vitro model for tumor suppression using angiogenic inhibitors, as well as an in vitro model for vasculitis, hypersensitivity and coagulation disorders.

Hematopoietic Cells:

Hematopoietic cells can be used to repopulate the bone marrow after high-dose chemotherapy. Hematopoietic cells derived from the cells of the aggregate can be further differentiated to form blood cells to be stored in blood banks, alleviating the problem of a limited supply of blood for transfusions.

Neuroectodermal Cells:

Microglial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. Cells induced to form oligodendrocytes and astrocytes, for example, can be used for transplant into demyelinated tissues, especially spinal cord, where they function to myelinate the surrounding nervous tissues. The cells also can be used in cell replacement therapy and/or gene therapy to treat congenital neurodegenerative disorders or storage disorders such as, for instance, mucopolysaccharidosis, leukodystrophies (globoid-cell leukodystrophy, Canavan's disease), fucosidosis, GM2 gangliosidosis, Niemann-Pick, Sanfilippo syndrome, Wolman's disease, and Tay Sachs. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

Ectodermal Epithelial Cells:

Cells can be used in cell replacement therapy and/or gene therapy to treat or alleviate symptoms of skin disorders such as alopecia, skin defects such as burn wounds, and albinism.

Endodermal Epithelial Cells:

Epithelial cells can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders, such as inborn errors of the urea-cycle, for instance ornithine decarboxylase deficiency, citrullinemia, and arginosuccinic aciduria; inborn errors of amino acids and organic acids, such as phenylketonuria, hereditary tyrosinemia, and alphal-antitrypsin deficiency; and coagulation disorders such as factor VIII and IX deficiency. The cells can also be used to treat acquired liver disorders that result from viral infections. The cells can also be used in ex vivo applications, such as to generate an artificial liver, to produce coagulation factors and to produce proteins or enzymes generated by liver epithelium. The epithelial cells can also be used in cell replacement therapy and/or gene therapy to treat or alleviate symptoms of biliary disorders, such as biliary cirrhosis and biliary atresia. The epithelial cells can also be used in cell replacement therapy and/or gene therapy to treat or alleviate symptoms of pancreatic disorders, such as pancreatic atresia, pancreas inflammation, and alphal-antitrypsin deficiency. Further, as pancreatic epithelium, and as neural cells can be made, beta-cells can be generated. These cells can be used for the therapy of diabetes (subcutaneous implantation or intra-pancreas or intra-liver implantation. Further, the epithelial cells can also be used in cell replacement therapy and/or gene therapy to treat or alleviate symptoms of gut epithelium disorders such as gut atresia, inflammatory bowel disorders, bowel infarcts, and bowel resection.

Cells are Useful for Tissue Repair:

Cells can also be used for tissue repair. Cells can be implanted into bone to enhance the repair process, to reinforce weakened bone, or to resurface joints. Chondrocytes can be injected into joints to resurface joint cartilage. Caplan et al. (U.S. Pat. No. 5,855,619) describe a biomatrix implant including a contracted gel matrix into which mesenchymal stem cells have been incorporated. The implant is designed for repair of a tissue defect, especially for injury to tendon, ligament, meniscus, or muscle. Cartilage, for example, can be formed by the addition of chondrocytes in the immediate area around a porous, 3-dimensional scaffold made, for example, of collagen, synthetic polyglycolic acid fibers, or synthetic polylactic fibers. The inventors have shown that cells of the present invention differentiate to form chondrocytes, for example, which can be deposited in and around a collagen, synthetic polyglycolic, or synthetic polylactic or other scaffold material to provide an implant to facilitate tissue repair.

Cells can be used to produce tissues or organs for transplantation. Oberpenning et al. (*Nature Biotechnology* 17:149-155 (1999)) reported the formation of a working bladder by culturing muscle cells from the exterior canine bladder and lining cells from the interior of the canine bladder, preparing sheets of tissue from these cultures, and coating a small polymer sphere with muscle cells on the outside and lining cells on the inside. The sphere was then inserted into a dog's urinary system, where it began to function as a bladder. Nicklason et al. (*Science* 284: 489-493 (1999)), reported the production of lengths of vascular graft material from cultured smooth muscle and endothelial cells. Other methods for forming tissue layers from cultured cells are known to those of skill in the art (see, for example, Vacanti et al., U.S. Pat. No. 5,855,610).

For the purposes described herein, autologous, allogeneic, or xenogeneic cells can be administered to a patient, either in differentiated or undifferentiated form, genetically altered or unaltered, by direct injection to a tissue site, systemically, on or around the surface of an acceptable matrix, or in combination with a pharmaceutically-acceptable carrier.

Model System for Studying Differentiation Pathways

The invention provides a method of using the aggregates or cells derived from the aggregates to characterize cellular responses to biologic or pharmacologic agents involving contacting the cells with one or more biologic or pharmacologic agents and identifying one or more cellular responses to the one or more biologic or pharmacologic agents. Such agents may have various activities. They could affect differentiation, metabolism, gene expression, viability, and the like. The cells are useful, therefore, for e.g., toxicity testing and identifying differentiation factors.

Cells of the present invention are useful for further research into developmental processes, as well. Ruley et al. (WO 98/40468), for example, have described vectors and methods for inhibiting expression of specific genes, as well as obtaining the DNA sequences of those inhibited genes. Cells of the present invention can be treated with the vectors such as those described by Ruley, which inhibit the expression of genes that can be identified by DNA sequence analysis. The cells can then be induced to differentiate and the effects of the altered genotype/phenotype can be characterized.

Hahn et al. (*Nature* 400: 464-468 (1999)) demonstrated, for example, that normal human epithelial fibroblast cells can be induced to undergo tumorigenic conversion when a combination of genes, previously correlated with cancer, were introduced into the cells.

Control of gene expression using vectors containing inducible expression elements provides a method for studying the effects of certain gene products upon cell differentiation. Inducible expression systems are known to those of skill in the art. One such system is the ecdysone-inducible system described by No et al. (*Proc. Natl. Acad. Sci. USA* 93:3346-3351 (1996).

Cells can be used to study the effects of specific genetic alterations, toxic substances, chemotherapeutic agents, or other agents on the developmental pathways. Tissue culture techniques known to those of skill in the art allow mass culture of hundreds of thousands of cell samples from different individuals, providing an opportunity to perform rapid screening of compounds suspected to be, for example, teratogenic or mutagenic.

For studying developmental pathways, cells can be treated with specific growth factors, cytokines, or other agents, including suspected teratogenic chemicals. Cells can also be genetically modified using methods and vectors known in the art. Furthermore, cells can be altered using antisense technology or treatment with proteins introduced into the cell to alter expression of native gene sequences. Signal peptide sequences, for example, can be used to introduce desired peptides or polypeptides into the cells. A particularly effective technique for introducing polypeptides and proteins into the cell has been described by Rojas, et al., in *Nature Biotechnology* 16:370-375 (1998). This method produces a polypeptide or protein product that can be introduced into the culture media and translocated across the cell membrane to the interior of the cell. Any number of proteins can be used in this manner to determine the effect of the target protein upon the differentiation of the cell. Alternately, the technique described by Phelan et al. (*Nature Biotech.* 16:440-443 (1998)) can be used to link the herpes virus protein VP22 to a functional protein for import into the cell.

Cells can also be genetically engineered, by the introduction of foreign DNA or by silencing or excising genomic DNA, to produce differentiated cells with a defective phenotype in order to test the effectiveness of potential chemotherapeutic agents or gene therapy vectors.

Kits

Cells can be provided in kits, with appropriate packaging material. For example, cells can be provided as frozen stocks, accompanied by separately packaged appropriate factors and media, as previously described herein, for culture in normal monolayer and/or as aggregates in the undifferentiated state. Additionally, separately packaged factors for induction of differentiation can also be provided.

Differentiation to Hepatic Phenotypes

The invention is also specifically directed to methods for culturing cells so that the cells are induced to differentiate into cells that express a hepatocyte phenotype and/or hepatocyte progenitor phenotype. More particularly, the invention relates to methods for culturing cells so that the cells are induced to differentiate into cells that express a definitive endodermal phenotype, a liver-committed endodermal phenotype, a hepatoblast phenotype, and hepatocyte phenotype. The invention is also directed to cells produced by the methods of the invention. The cells are useful, among other things, for treatment of liver deficiency, liver metabolism studies, and liver toxicity studies. Culture methods are described in PCT/US08/82108, incorporated herein by reference for teaching these methods. Specific culture conditions are, for example, as in the following numbered statements:

1. A method for inducing cells to differentiate into cells with a hepatocyte phenotype, comprising:
   (a) culturing cells with about 5 ng/ml to about 500 ng/ml Wnt3a and about 10 ng/ml to about 1,000 ng/ml ActivinA;
   (b) then culturing the cells of step (a) with about 1 ng/ml to about 100 ng/ml bFGF and about 5 ng/ml to about 500 ng/ml BMP4;
   (c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b; and
   (d) then culturing the cells of step (c) with about 2 ng/ml to about 200 ng/ml HGF and about 10 ng/ml to about 1,000 ng/ml Follistatin.

2. The method of statement 1, wherein the cells are cultured in step (a) with about 50 ng/ml Wnt3a and about 100 ng/ml ActivinA.

3. The method of statement 1, wherein the cells are cultured in step (b) with about 10 ng/ml bFGF and about 50 ng/ml BMP4.

4. The method of statement 1, wherein the cells are cultured in step (c) with about 50 ng/ml aFGF, about 10 ng/ml FGF4 and about 25 ng/ml FGF8b.

5. The method of statement 1, wherein the cells are cultured in step (d) with about 20 ng/ml HGF and about 100 ng/ml Follistatin.

6. A method for inducing cells to differentiate into cells with a hepatocyte phenotype, comprising:
   (a) culturing the cells with about 50 ng/ml Wnt3a and about 100 ng/ml ActivinA;
   (b) then culturing the cells of step (a) with about 10 ng/ml bFGF and about 50 ng/ml BMP4;
   (c) then culturing the cells of step (b) with about 50 ng/ml aFGF, about 10 ng/ml FGF4 and about 25 ng/ml FGF8b; and
   (d) then culturing the cells of step (c) with about 20 ng/ml HGF and about 100 ng/ml Follistatin.

The starting cells can have a primitive endodermal phenotype. Subsequent steps (a)-(d) can produce cells with definitive endodermal phenotype, liver-committed phenotype, hepatoblast phenotype, and hepatocyte phenotype, respectively.

7. The methods above, wherein the cells are cultured at one or more steps in a medium containing a serum concentration ranging from 0% to about 2%.

8. The method of statement 7, wherein the cells are cultured at one or more steps in a medium containing a serum concentration of about 2%.

9. The methods above, wherein the cells are cultured at one or more steps in a medium containing about $10^{-4}$ M to about $10^{-7}$ M dexamethasone.

10. The method of statement 9, wherein the cells are cultured at one or more steps in a medium containing about $10^{-6}$ M dexamethasone.

11. The methods above, wherein the cells are cultured at one or more steps for at least four days.

12. The method of statements above, wherein the cells that express a primitive endodermal phenotype are cultured for about six days, the cells that express a definitive endodermal phenotype are cultured for about four days, the cells that express a liver-committed endodermal phenotype are cultured for about four days, and the cells that express a hepatoblast phenotype are cultured for about seven days.

Accordingly the invention is also directed to methods of treating liver deficiencies by administering the cells of the invention to a subject with the liver deficiency. Such deficiencies include, but are not limited to, toxic liver disease, metabolic liver disease, acute liver necrosis, effects of acetaminophen, hemochromatosis, Wilson's Disease, Crigler Najar, hereditary tyrosinemia, familial intrahepatic cholestatis type 3, ornithine transcarbamylase (OTC) deficiency, and urea cycle disorder.

Further diseases include, but are not limited to, viral hepatitis, chronic viral hepatitis A, B, C, acute hepatitis A, B, C, D, E, cytomegalovirus and herpes simplex virus; liver dysfunction in other infectious diseases such as, without limitation, toxoplasmosis, hepatosplenic schistosomiasis, liver disease in syphilis, leptospirosis and amoebiasis; metabolic diseases such as, without limitation, haemochromatosis, Gilbert's syndrome, Dubin-Johnson syndrome and Rotor's syndrome; alcoholic liver disease such as, without limitation, fatty liver, fibrosis, sclerosis and cirrhosis; and toxic liver disease.

The invention will be further described by reference to the following detailed examples.

EXAMPLES

Example 1. Self-Assembly of Multipotent Adult Progenitor Cells (MAPCs) and Differentiation to the Hepatic Lineage Background Earlier studies have shown that spheroidal aggregate (3D) culture of primary hepatocytes results in the maintenance of viability and enhancement of liver specific functions over a long culture period. MAPC isolated from postnatal rat, mouse, and human bone marrow can be expanded in vitro in 2D culture without senescence and can differentiate into cells with morphological, phenotypic, and functional characteristics of hepatocytes. The inventors investigated the possibility that MAPCs could self-assemble into 3D aggregates and differentiate into hepatocytes. MAPCs were successfully induced into 3D aggregates that exhibited good viability, morphology and differentiation potential based on expression of several endoderm markers like HNF3b, AFP, AAT, TTR and albumin. Differentiation protocols for making cells with hepatic phenotypes has use in cell therapies. Other applications include use in drug toxicity studies, bioartificial liver support, tissue engineering, and as a model system to study development and disease.

A four-step 21-day differentiation protocol was described above, optimized for medium components, oxygen levels and extra-cellular matrix for efficient differentiation to cells with morphological, phenotypic, and functional characteristics of hepatocytes from MAPCs. Time-dependent expression of endoderm genes was observed, including Goosecoid, CXCR4 and EINF3b early representing the progression through definitive endoderm, followed by AFP and transthyretin corresponding to the onset of hepatic specification, and expression of albumin, glucose 6 phosphatase (G6P), and cytochrome P450 depicting maturation at levels expressed in fetal liver by the end of differentiation. In addition to gene expression, protein level expression of differentiated cells was also observed by immunohistochemistry for HNF3b, AFP, CK18 and albumin and their functional nature evaluated by albumin ELISA and PAS staining for glycogen storage.

Following this differentiation of MAPCs in 2D monolayer, the inventors investigated the ability of MAPCs to self-assemble into 3D aggregates and explored the possibility of enhanced differentiation. MAPCs were successfully induced into 3D aggregates that exhibited good viability, morphology, and undifferentiated phenotype in terms of expression of high levels of oct3/4 and lack of expression of differentiated markers when formed under "MAPC media" and 5% oxygen. The aggregates retained the ability to undergo spontaneous multi-lineage differentiation as well as directed differentiation to the hepatic lineage with improved expression of HNF4a, a transcription factor, DPPIV, a bile duct protein, and CYP2B1 and G6P, functional hepatic markers in 3D compared to their expression in corresponding 2D differentiation. Other than the advantage of obtaining more functionally mature differentiated cells, 3D culture provides a unique model system for studying nascent 3D development and can potentially help in the design of scalable culture systems that can be monitored and controlled to enhance differentiation.

Liver cell transplantation and cellular-based therapies are emerging as viable clinical alternatives to whole organ transplantation as treatment therapies for acute, chronic and metabolic liver diseases. Several stem or progenitor cells have been identified from bone marrow, peripheral blood, cord blood, fetal and adult liver, and embryonic stem cells with the potential to proliferate and differentiate into 'hepatocyte-like' cells in vitro or in vivo. Multipotent Adult Progenitor Cells (MAPCs) isolated from postnatal rat, mouse and human bone marrow can be expanded in vitro without senescence, differentiate in vitro and in vivo, at the single cell level, into different cell types of the three germ layer lineages. MAPCs have the advantage of not forming teratomas when transplanted and can be selected from autologous bone marrow without the need for immunosuppression.

Although MAPCs have been shown to differentiate in vitro into albumin$^+$CK18$^+$ epithelial cells that secrete albumin and urea, these 'hepatocyte-like' cells are not fully differentiated, and cultures continue to have mixed heterogeneous population of cells. Several studies have shown that spheroidal aggregate (3D) culture of primary hepatocytes resulted in enhancement of liver specific functions over a long culture period. The inventors investigated the ability of MAPCs to self-assemble into 3D aggregates and explored the possibility of differentiation to the hepatic lineage.

Differentiation of MAPCs to the hepatic lineage occurs as a result of sequential array of distinct biological events similar to modular liver development during embryogenesis. A differentiation program of 20 days in four consecutive steps can be applied including, formation of the definitive endoderm, specification of the ventral foregut endoderm, enrichment of bi-potential hepatic progenitors or hepatoblasts, and maturation into functional 'hepatocyte-like' cells. On treating the cells with a high dexamethasone and serum-free differentiation basal media containing Activin A and Wnt-3a for a period of 6 days, bFGF and BMP4 between days 6-10, aFGF, FG8b and FGF4 between days 10-14 and HGF and Follistatin for the final period between 14-21 days, definitive endoderm markers like Goosecoid and CXCR4 were transiently expressed in the first stage and progressive increase in several endoderm markers including, α-fetoprotein (AFP), transthyretin (TTR), albumin, α-1 antitrypsin (AAT), tyrosine aminotransferase (TAT), arginase-1 and glucose-6-phosphatase were observed at the mRNA level. Further, albumin ELISA revealed increasing albumin levels in the medium with time, the protein level expression of albumin, AFP and CK18 were confirmed by immunohistochemistry, and glycogen storage was observed by PAS staining. There was also evidence of the above protocol's applicability in the differentiation of human embryonic stem cells to cells expressing AFP, TTR and albumin at the mRNA level. Although there is evidence for existence of some cells with the mature hepatocyte phenotype in the differentiation cultures, the persistent expression of AFP and CK19 at later stages of differentiation and the expression of mesodermal transcripts like Ve-Cadherin (endothelial cell marker) and SM22 (smooth muscle marker) indicates the existence of a mixed population of mesodermal cell types and 'hepatocyte-like' cells at different stages of maturity. Hence, it is was the inventors' interest to investigate the potential of three-dimensional (3D) culture systems to facilitate the maturation of the hepatocyte precursors and the utilization of promoter-reporter constructs for the selection of mature hepatocytes or immature precursors from the heterogeneous cell population.

Accordingly, the inventors identified conditions for optimal growth of undifferentiated MAPCs in 3D spherical clusters and assessed their differentiation potential to several cell types, specifically of the endodermal lineage. They found that undifferentiated MAPCs form 3D aggregates in culture and that the 3D aggregates retain the capacity to differentiate.

Experiment

Rat MAPC clones expressing high levels of oct3/4 were used for formation of MAPC aggregates using either the hanging drop method (surface tension driven) or the forced aggregation method (centrifugation) over a period of 4 days using MAPC media, MAPC media without LIF (leukemia inhibitory factor), or differentiation basal media in both low and high oxygen conditions. The starting cell number between 400-4000 cells/well was used in both the methods. Upon characterization of the MAPC aggregates formed using flow cytometry and quantitative real time polymerase chain reaction (QRT-PCR), MAPC media with LIF and low oxygen condition was optimum as oct3/4 mRNA expression levels was equivalent between MAPCs before and after aggregate formation and almost 90% of the number of cells expressing in MAPCs (~79%) before aggregate formation expressed oct3/4 at the protein level after formation of aggregates (~69%). Further, the oct3/4 mRNA levels were comparable between aggregates formed using the hanging drop method or the forced aggregation method. The aggregates also expressed GATA6, HNF3b and Goosecoid at levels that are comparable to expression levels in MAPCs and did not show any expression of differentiation markers like AFP, albumin, AAT and TAT. Upon spontaneous differentiation in differentiation basal media (upon removal of LIF, PDGF and EGF), the cell aggregates underwent spontaneous differentiation to express Nestin and Pax6 corresponding to neuroectoderm, Flk-1 and SM22 corresponding to mesoderm and AFP and Albumin corresponding to the endoderm germ layer. Although all of the above work was using rat high-oct3/4 expressing MAPCs, low-oct3/4 rat MAPCs also formed aggregates with the ability to undergo differentiation to several cell types. There is also evidence of 3D aggregates from mouse MAPC clones that also retained the expression of oct3/4 in the aggregates and subsequently underwent spontaneous differentiation upon transfer to differentiation basal media.

Upon differentiation of rat high oct3/4 MAPC aggregates using the protocol optimized earlier for hepatocyte differentiation, the outcome of differentiation was comparable to high density 2D differentiation that was performed at the same time based on expression of hepatic markers like albumin, AFP, TTR, AAT and TAT. Therefore, it is apparent that the 3D aggregates are capable of undergoing significant levels of differentiation to the hepatic lineage starting from a 'MAPC-like' phenotype.

Functional and structural properties of the differentiated aggregates: albumin ELISA for estimating albumin secretion rates, PAS staining for glycogen storage, immunostaining investigating the polarization into basal, apical and lateral domains and elucidating the ultra-structural characteristics using transmission electron microscopy (TEM). In addition, the use of these oct3/4 expressing MAPC aggregates as a potential method for scalable expansion of MAPCs also was explored.

Materials and Methods

"MAPC Media"

MAPC media contained 60% (v/v) low glucose Dulbecco's Modified Eagle Media (DMEM) (11885, Gibco BRL, Carlsbad, Calif., USA), 40% (v/v) MCDB-201 (M6770, Sigma), 1% (v/v) 1× insulin-transferrin-selenium (ITS; Sigma), 1% (v/v) 1× linoleic acid bovine serum albumin (LA-BSA; Sigma), $5 \times 10^{-8}$ M dexamethasone (Sigma), $10^{-4}$ M ascorbic acid 3-phosphate (Sigma), 100 units of penicillin, 1000 units of streptomycin, 2% (v/v) fetal bovine serum (FBS; Hyclone, Logan, Utah, USA), 10 ng/ml mouse epidermal growth factor (Sigma), 10 ng/ml human platelet derived growth factor (R&D systems, Minneapolis, Minn., USA), 0.54% 1× β-mercaptoethanol and 1000 units/ml mouse leukemia inhibitory factor. Media was sterilized using a 22-μm filter (Millipore, Billerica, Mass., USA) and was kept at 4° C. for a maximum of 3-4 weeks. Formation of MAPC Aggregates MAPC aggregates were formed by using either the Hanging drop method or the forced aggregation method. In the Hanging drop method; MAPCs were seeded at 100-4000 cells/well of a 60-well microtitre plate (Nunc) in 20 μl of MAPC medium/well. The plates were then inverted and placed in 5% oxygen 37 C incubator for 4-5 days for the aggregates to form. In the forced aggregation method, 100-4000 MAPCs/well of a 96 well U bottom Ultra-low attachment plate (Corning) were centrifuged at 1500 rpm, 4 minutes and the cells were allowed to aggregate in a 5% oxygen 37 C incubator over the next 4-5 days.

Differentiation of MAPC Aggregates

There recently was developed a four-step, 21-day differentiation protocol optimized for medium components, oxygen levels and extra-cellular matrix for efficient differentiation to cells with morphological, phenotypic and functional characteristics of hepatocytes from MAPCs. The four-step protocol consisted of the following: (1) culturing MAPCs with 50 ng/ml Wnt3a and 100 ng/ml Activin A for six days; (2) then culturing the cells from step (1) with 10 ng/ml bFGF and 50 ng/ml BMP4 for four days; (3) then culturing the cells from step (2) with 50 ng/ml aFGF, 10 ng/ml FGF4 and 25 ng/ml FGF8b for four days; and (4) then culturing the cells from step (3) with 20 ng/ml HGF and 100 ng/ml Follistatin for seven days. In order to discriminate between hepatocyte- or biliary-like cells, Activin was inhibited by Follistatin. Prior to differentiation of the cells, undifferentiated MAPCs were expanded at large scale until several million cells were obtained. Cells then were plated at 50,000-60,000 cells/cm$^2$ in Matrigel (2%) coated wells. Initially, cells were cultured in expansion medium until they reached 80-90% confluency 16 hours later. Then, cells were washed twice with PBS and the medium was switched to differentiation medium. To verify whether the addition of the cytokines had a real hepatocyte inducing effect, differentiation was performed using basal differentiation medium only. All cells were cultured in low oxygen (5%) conditions in the basal differentiation medium, which consisted of DMEM (60%), MCDB (40%), ascorbic acid (IX), penicillin/streptomycin (1×), beta-mercaptoethanol, insulin-transferrin-selenium (ITS) (0.25×), LA-BSA (0.25×) and dexamethasone ($10^{-6}$ M). A high concentration of dexamethasone was used because some hepatocyte specific genes (i.e., tyrosine aminotransferase, MRP2 and tryptophan 2,3 dioxygenase) are upregulated by glucocorticoids, as they contain a glucocorticoid response element. In the complete absence of serum, cell death occurred. However, using Wnt3a, differentiation was induced in serum-free conditions. If no cytokines were added to the basal differentiating medium, 2% serum was added until day 12 and then stopped. Because high concentrations of dexamethasone, together with insulin, can induce adipogenesis, a lower amount of insulin was used.

Figure 11A:
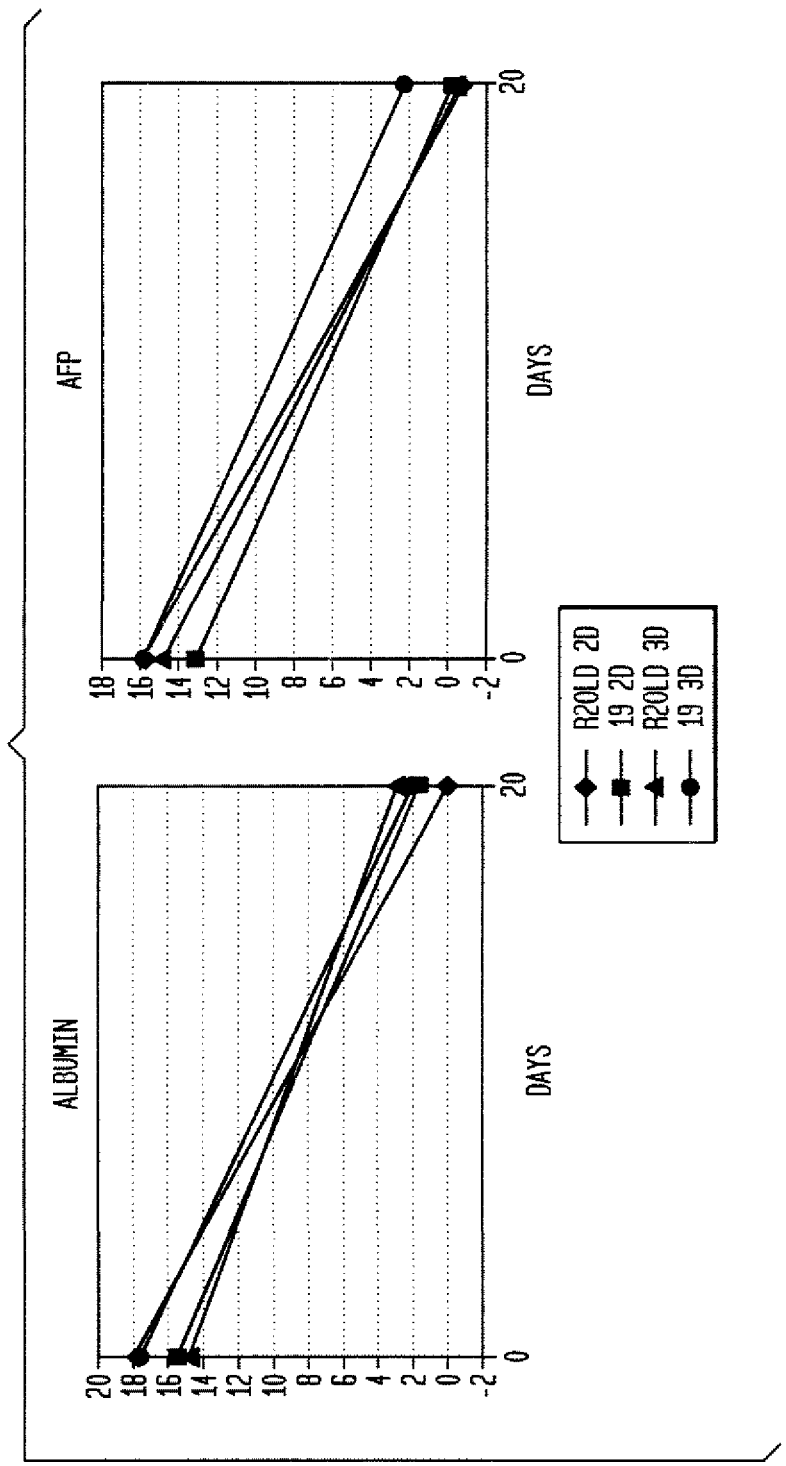
FIG. 11 shows directed differentiation to hepatocytes (A), endothelial cells (B), and neural precursors (C), starting from rat MAPC lines R2old and 19 maintained undifferentiated in 2D vs. 3D conditions.
Figure 11B:
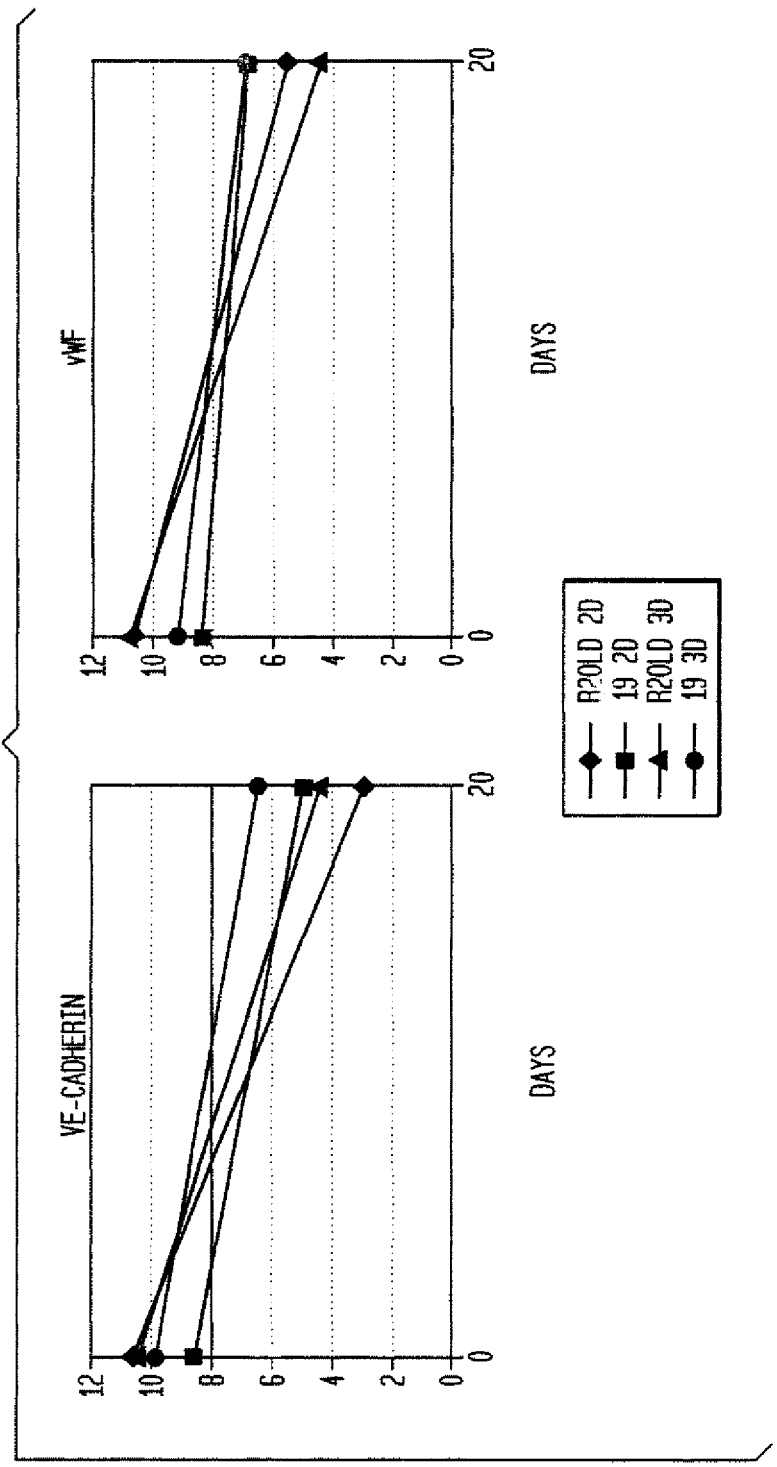
Figure 11C:
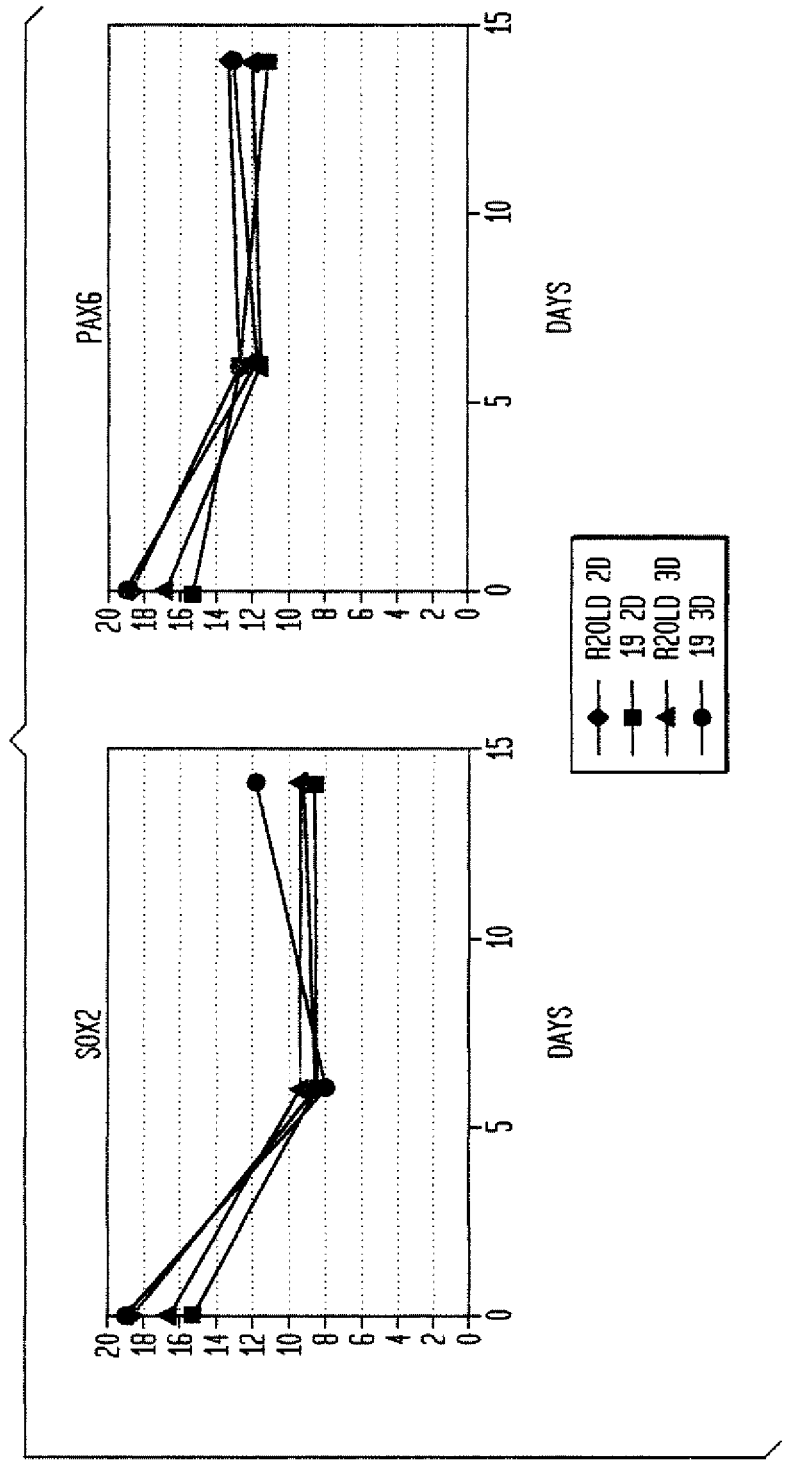

Example 2. Comparison of Differentiation of Rat MAPC Lines R2Old and 19 Under 2D and 3D Conditions The goal of this study was to demonstrate the multi-lineage differentiation capability of MAPCs when grown and cultured as 3D aggregates. Two lines of rat MAPCs: R2old and 19, were used and were maintained for a period of 16 days as 3D aggregates in MAPC maintenance conditions:

MAPC media with 5% oxygen. At the end of the 16 day period, 3D aggregates were dissociated and replated onto fibronectin-coated dishes, similar to standard 2D monolayer maintenance of rat MAPCs. Subsequently, growth factor mediated differentiation to hepatocytes, endothelial cells and neural precursor cells were performed and the differentiations were compared to differentiations of rat MAPCs that were maintained in 2D monolayer culture during the same time period. The data in FIGS. 11 (A), (B) and (C) indicate the expression of markers corresponding to the different cell types, by Quantitative-real time (QRT)-PCR. From the data, it appeared that the cells maintained as 3D aggregates retained the potential to undergo multi-lineage differentiation at levels comparable to cells maintained in 2D culture. Thus, MAPCs could be maintained in 3D culture without loss of quality, thus making it amenable to scale-up in bioreactors.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method comprising (1) disaggregating cells in an aggregate, the aggregate having been formed by exposing cells that are not embryonic stem cells, embryonic germ cells, or germ cells and can differentiate into cell types of at least two of the endodermal, ectodermal, mesodermal embryonic lineages, to conditions under which the cells aggregate, wherein the conditions comprise an oxygen concentration of about 1-10%, wherein the aggregate from which the disaggregated cells are derived does not originate from two-dimensional culture and (2) administering to a subject, in an amount and for a time sufficient to achieve a desired effect in the subject, the cells derived from disaggregating the aggregate of cells.

2. The method of claim 1, wherein cells are aggregated by the hanging drop method or forced aggregation method.

3. The method of claim 1, wherein the aggregation of the aggregate is carried out in cell culture.

4. The method of claim 1, wherein cells in the aggregate and cells derived from the aggregate express one or more of Oct 3/4, telomerase, rex-1, rox-1, nanog, GATA6 and sox-2.

5. The method of claim 1 or 4, wherein cells in the aggregate and cells derived from the aggregate can differentiate into cell types of all three of the endodermal, ectodermal and mesodermal embryonic lineages.

6. The method of claim 1, wherein the aggregate contains about 10 cells to about 50,000 cells or more.

7. The method of claim 1, wherein the aggregate contains about 1000 cells to about 5000 cells.

8. The method of claim 1 or 4, wherein the non-embryonic stem, non-embryonic germ, non-germ cells are derived from bone marrow.

9. The method of claim 5, wherein the non-embryonic stem, non-embryonic germ, non-germ cells are derived from bone marrow.

10. The method of claim 8, wherein the non-embryonic stem, non-germ cells are human cells.

11. The method of claim 9, wherein the non-embryonic stem, non-germ cells are human cells.

12. The method of claim 1 or 4 further comprising admixing the disaggregated cells with a pharmaceutically-acceptable vehicle for administration to a subject.

* * * * *

UNITED STATES PATENT AND TRADEMARK OFFICE
CERTIFICATE OF CORRECTION

Page 1 of 1

PATENT NO. : 10,253,297 B2
APPLICATION NO. : 13/889015
DATED : April 9, 2019
INVENTOR(S) : Hu et al.

It is certified that error appears in the above-identified patent and that said Letters Patent is hereby corrected as shown below:

On the Title Page

Item (57) Abstract, Line 5:
The word(s) "undo dermal" should read --endodermal--

Signed and Sealed this
Thirty-first Day of March, 2020

Andrei Iancu
*Director of the United States Patent and Trademark Office*